US008071818B2

(12) United States Patent
Jenkins

(10) Patent No.: US 8,071,818 B2
(45) Date of Patent: Dec. 6, 2011

(54) THERAPEUTIC COMPOUNDS

(75) Inventor: Thomas E. Jenkins, San Carlos, CA (US)

(73) Assignee: PharmacoFore, Inc., San Carlos, CA (US)

( * ) Notice: Subject to any disclaimer, the term of this patent is extended or adjusted under 35 U.S.C. 154(b) by 0 days.

(21) Appl. No.: 12/596,800

(22) PCT Filed: May 8, 2008

(86) PCT No.: PCT/US2008/063082
§ 371 (c)(1),
(2), (4) Date: May 28, 2010

(87) PCT Pub. No.: WO2008/141097
PCT Pub. Date: Nov. 20, 2008

(65) Prior Publication Data
US 2010/0292346 A1 Nov. 18, 2010

Related U.S. Application Data

(60) Provisional application No. 60/928,296, filed on May 9, 2007, provisional application No. 60/928,429, filed on May 9, 2007, provisional application No. 60/928,327, filed on May 9, 2007.

(51) Int. Cl.
C07C 39/24 (2006.01)
C07C 39/06 (2006.01)
A61K 31/05 (2006.01)
(52) U.S. Cl. ........ 568/775; 568/778; 568/780; 514/731; 514/737
(58) Field of Classification Search .................. 568/775, 568/778, 780; 514/731, 737
See application file for complete search history.

(56) References Cited

U.S. PATENT DOCUMENTS

| | | | |
|---|---|---|---|
| 2,747,982 A | 5/1956 | Mussell et al. |
| 4,056,635 A | 11/1977 | Glen et al. |
| 4,452,817 A | 6/1984 | Glen et al. |
| 4,798,846 A | 1/1989 | Glen et al. |
| 5,714,520 A | 2/1998 | Jones et al. |
| 5,731,355 A | 3/1998 | Jones et al. |
| 5,908,869 A | 6/1999 | Jones et al. |
| 6,140,374 A | 10/2000 | May et al. |
| 7,731,356 B1 | 6/2010 | Gilbert |

FOREIGN PATENT DOCUMENTS

WO 2006033911 3/2006

OTHER PUBLICATIONS

Voss, Guenther, Substituted phenyl N-methylcarbamate. Cholinesterase inhibition and insecticidal activity. Anzeiger fuer Schaedlingskunde, 1967, vol. 40 (5), 73-77. HCAPLUS document No. 67:81442; Accession No. 1967:481442.*

James, et al. Synthesis, Biological Evaluation, and Preliminary Structure-Activity Considerations of a Series of Alkylphenols as Intravenous Anesthetic Agents. J. Med. Chem. 1980, 23, 1350-1357.
Krasowski, et al. General Anesthetic Potencies of a Series of Propofol Analogs Correlate with Potency for Potentiation of gamma-Aminobutyric Acid (GABA) Current at the GABA-A receptor but Not with Lipid Solubility. Journal of Pharmacology and Experimental Therapeutics, American Society for Pharmacology and Experimental Therapeutics, US, vol. 297, No. 1, (2001), pp. 338-351.
Maciagiewicz, et al. Design and synthesis of propofol analogs as new anesthetic agents. Abstracts of Papers, 233rd ACS National Meeting, Chicago, IL, United States, Mar. 25-29, 2007 (2002).
Altomare et al., "Highly Water-Soluble Derivatives of the Anesthetic Agent Propofol: In Vitro and In Vivo Evaluation of Cyclic Amino Acid Esters" Eur J Pharm Sci., vol. 20, (2003), p. 17-26.
Concas et al. "The General Anesthetic Propofol Enhances the Function of Gamma-Aminobutyric Acid-Coupled Chloride Channel in the Rat Cerebral Cortex" Journal of neurochemistry, vol. 55 (1990), p. 2135-2138.
Concas et al., "Neurochemical Action of the General Anaesthetic Propofol on the Chloride Ion Channel Coupled with GABAA Receptors" BRES, vol. 16356, (1990), p. 225-232.
Fechner et al. "Comparative Pharmacokinetics and Pharmacodynamics of the New Propofol Prodrug GPI 15715 and Propofol Emulsion" Anesthesiology, vol. 101, (2004), p. 626-639.
Fechner et al. "Pharmacokinetics and Clinical Pharmacodynamics of the New Propofol Prodrug GPI 15715 in Volunteers" Anesthesiology, vol. 99 (2003), p. 303-313.
Fechner et al. "Sedation with GPI 15715, a Water-Soluble Prodrug of Propofol, Using Target-Controlled Infusion in Volunteers" Anesthesia and Analgesia, vol. 100, (2005), p. 701-706.
Jian Qiu et al. "2,6-Difluorophenol as a Bioisostere of a Carboxylic Acid: Bioisosteric Analogues of y-Aminobutyric Acid" J. Med. Chem., vol. 42, (1999), p. 329-332.
Sagara et al. "Propofol Hemisuccinate Protects Neuronal Cells From Oxidative Injury" J Neurochem., vol. 73(6), (1999), p. 2524-2530.
Sanna E et al. "Novel Properties of Homomeric,81 -y-Aminobutyric Acid Type A Receptors: Actions of the Anesthetics Propofol and Pentobarbital" Molecular Pharmacology, vol. 47, (1995), p. 213-217.
Sneyd, J.R. "Recent Advances in Intravenous Anaesthesia" Br J Anaesth, vol. 93, (2004), p. 725-736.
Struys et al. "AQUAVAN Injection, a Water-Soluble Prodrug of Propofol, as a Bolus Injection: a Phase I dose-Escalation Comparison with DIPRIVAN (part 2): Pharmacodynamics and Safety" Anesthesiology, vol. 103, (2005), p. 730-743.

(Continued)

Primary Examiner — Sikarl Witherspoon
(74) Attorney, Agent, or Firm — Connie C. Tong; Carol L. Francis; Bozicevic, Field & Francis LLP

(57) ABSTRACT

A (−)-stereoisomer of formula (I): [insert formula (I) wherein X is H or F; or a pharmaceutically acceptable salt or prodrug thereof, useful as an anesthetic.

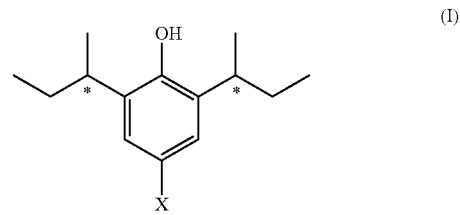

37 Claims, 2 Drawing Sheets

OTHER PUBLICATIONS

Tan, et al. "Pain on Injection of Propofol" Anaesthesia, vol. 53, (1998) p. 468-476.
Thompson Sally-Anne et al. "Mechanism of Action of General Anaesthetics New Information from Molecular Pharmacology" Current Opinion in Pharmaologym, vol. 1 (2001), p. 78-83.
Tomlin, S.L..et al. "Stereoselective Effects of Etomidate Optical Isomers on Gamma Aminobutyric Acid Type A Receptors and Animals" Anesthesiology, vol. 88, (1998), p. 708-717.
Trapani, G.et al. "Propofol in Anesthesia. Mechanism of Action, Structure-Activity Relationships, and Drug Delivery" Current Medicinal Chemistry, vol. 7, (2000) p. 249-271.
Trapani, G. et al. "Propofol Analogues. Synthesis, Relationships between Structure and Affinity at GABAA Receptor in Rat Brain, and Differential Electrophysiological Profile at Recombinant Human GABBA Receptors" J Med Chem, vol. 41, (1998), p. 1846-1854.
Adams et al. "Propofol-Induced Injection Pain: Comparison of a Modified Propofol Emulsion to Standard Propofol with Premixed Lidocaine" Anesthesia and Analgesia, vol. 99, (2004), p. 1076-1079.
Baker et al. "Propofol: the challenges of formulation" Anesthesiology, vol. 103, (2005), p. 860-876.
Bocian et al, "Propofol (Diprivan)1_A New Intravenous Anesthetic with Applications for Outpatient Ambulatory Surgery" the journal of foot surgery, vol. 31 (1992) p. 603-606.
Bruce et al. "Oxidative Coupling of Some 2,6-Disubstituted Phenols" Polymer, vol. 10(8), (1969), p. 701-705.
Bryson Harriet M. et al. "Propofol: An Update of its Use in Anaesthesia and Conscious Sedation" Drugs, vol. 60, (1995) p. 613-669.
Doenicke, A.W. et al. "Reducing Pain During Propofol Injection: The Role of the Solvent" Anesth Analg, vol. 82, (1996), p. 472-474.
Doenicke et al. "Pharmacokinetics and Pharmacodynamics of Propofol in a New Solvent" Anesth Analg, vol. 85, (1997), p. 1399-1403.
Dubey, P.K. et al. "Pain on Injection of Lipid-Free Propofol and Propofol Emulsion Containing Medium-Chain Triglyceride: A Comparative study" Anesthesia and Analgesia, vol. 101, (2005), p. 1060-2, table of contents.
Fulton Bret et al. "Propofol: A Pharmacoeconomic Appraisal of its Use in Day Case Surgery" PharmacoEconomics, vol. 9, (1996), p. 168-178.
Fulton Bret et al. "Propofol: An Overview of its Pharmacology and a Review of its Clinical Efficacy in Intensive Care Sedation" Drugs, vol. 50, (1995), p. 636-667.
Gabel, Ronald A. "Sedation/Analgesia—An Anesthesiologist's Perspective" (2002).
Glen, J.B. et al. "Pharmacology of an Emulsion Formulation of ICI 35 868" British Journal of Anaesthesia, vol. 56, (1984), p. 617-626.
Kam, E. et al. "Comparison of Propofol-Lipuro with Propofol Mixed with Lidocaine 10 mg on Propofol Injection Pain" Anaesthesia, vol. 59, (2004), p. 1167-1169.
Kanto J. et al. "Pharmacokinetic Implications for the Clinical Use of Propofol" Clinical Pharmacokinetics, vol. 17, (1989), p. 308-326.
Klement, W. et al "Pain on Injection of Propofol: Effects of Concentration and Diluent" Br J Anaesth, vol. 67, (1991), p. 281-284.
Larijani Ghassem E. et al. "Clinical Pharmacology of Propofol: An Intravenous Anesthetic Agent" DICP The Annals of Pharmacotherapy, vol. 23, (1989), p. 743-749.
Maleck W. H. "Propofol Induced Injection Pain: Comparison of a Modified Propofol Emulsion and Standard Propofol with Premixed Lidocaine" Anesth Analg, vol. 70, (2005), p. 100:1858.
Marinella M.A. "Propofol for Sedation in the Intensive Care Unit: Essentials for the Clinician" Repiratory Medicine, vol. 91, (1997), p. 505-510.
Miller "Effects on the Central Nervous System" Millers Anesthesia, (2005), p. 320-370.
Nathanson, M.H. et al. "Prevention of Pain on Injection of Propofol: A Comparison of Lidocaine with Alfentanil" Anesthesia and Analgesia, vol. 82, (1996), p. 469-471.
Nolan J. et al. "Pharmacokinetic of Propofol Administered by Infusion in Dogs Undergoing Surgery" British Journal of Anaesthesia, vol. 70, (1993), p. 546-551.
Nyman, Y. et al. "Propofol Injection Pain in Children: A Prospective Randomized Double Blind Trial of a New Propofol Formulation Versus Propofol with Added Lidocaine" British Journal of Anaesthesia, vol. 95, (2005), p. 222-225.
Ohmizo, H. et al. "Mechanism of Injection Pain with Long and Long-Medium Chain Triglyceride Emulsive Propofol" Canadian Journal of Anaesthesia [Journal Canadien d'Anesthesie], vol. 52, (2005), p. 595-599.
Parmar, A.K. et al. "Pain on Injection of Propofol. A Comparison of Cold Propofol with Propofol Premixed with Lignocaine" Anaesthesia, vol. 53, (1998), p. 79-83.
Paul, M. et al. "Pharmacological Characteristics and Side Effects of a New Galenic Formulation of Propofol without Soyabean Oil" Anaesthesia, vol. 58, (2003), p. 1056-1062.
Picard, P. et al. "Prevention of Pain on Injection with Propofol: a Quantitative Systematic Review" Anesthesia and Analgesia, vol. 90, (2000), p. 963-969.
Rau, J. et al. "Propofol in an Emulsion of Long- and Medium-Chain Triglycerides: the Effect on Pain" Anesth Analg, vol. 93, (2001), p. 382-4 3rd contents p. 38.
Reich, D.L. et al. "Predictors of Hypotension after Induction of General Anesthesia" Anesthesia and Analgesia, vol. 101, (2005), p. 622-628.
Schaub, E. et al. "Pain on Injection: A Double-Blind Comparison of Propofol with Lidocaine Pretreatment Versus Propofol Formulated with Long- and Medium-Chain Triglycerides" Anesthesia and Analgesia, vol. 99, (2004), p. 1699-702, table of contents.
Shafer Steven L. "Advances in Propofol Pharmacokinetics and Pharmacodynamics" Journal of clinical anesthesia, vol. 5, (1993), p. 14-21.
Soltesz, S. et al. "Effect of a 0.5% Dilution of Propofol on Pain on Injection during Induction of Anesthesia in Children" Anesthesiology, vol. 106 (2007) p. 80-84.
Sun, et al. "A Comparison of Pain on Intravenous Injection between Two Preparations of Propofo" Anesthesia and analgesia, vol. 101, (2005), p. 675-8, table of contents.
Suzuki, H. et al. "Propofol Formulated with Long-/Medium-Chain Triglycerides Reduces the Pain of Injection by Target Controlled Infusion" Acta anaesthesiologica Scandinavica, vol. 50, (2006), p. 568-571.
Tan, C.H. et al. "The Effect of Ketamine Pretreatment on Propofol Injection Pain in 100 Women" Anaesthesia, vol. 53 (1998) p. 302-305.
Ueki, R. et al."Emulsion of Flurbiprofen Axetil Reduces Propofol Injection Pain Due to a Decrease in Free Propofol Concentration" Journal of Anesthesia, vol. 21, (2007), p. 325-329.
White Paul F. "Propofol: Pharmacokinetics and Pharmacodynamics" Seminars in Anesthesia, vol. 7, Apr. 20, 1988.
Wong, W.H. et al. "Role of Tramadol in Reducing Pain on Propofol Injection", Singapore Medical Journal, vol. 42, (2001), p. 193-195.
Wouters, P.F. et al. "Hemodynamic Changes during Induction of Anesthesia with Eltanolone and Propofol in Dogs" Anesthesia and Analgesia, vol. 81, (1995), p. 125-131.
Yamakage, M. et al. "Changes in Concentrations of Free Propofol by Modification of the Solution" Anesthesia and Analgesia,vol. 101, (2005), p. 385-8, table of contents.
Zeller, A. et al. "Distinct Molecular Targets for the Central Respiratory and Cardiac Actions of The General Anesthetics Etomidate and Propofol" The FASEB journal, vol. 19, (2005), p. 1677-1679.

\* cited by examiner

THERAPEUTIC COMPOUNDS

The present application claims the benefit of U.S. provisional patent application No. 60/928,327 filed on May 9, 2007; U.S. provisional patent application No. 60/928,429 filed on May 9, 2007 and U.S. provisional patent application No. 60/928,296 filed on May 9, 2007.

BACKGROUND OF THE INVENTION

Propofol (2,6-diisopropylphenol) is an intravenous sedative/hypnotic agent used extensively for induction and maintenance of general anesthesia, sedation of critically ill patients and procedural sedation (e.g., endoscopy). See Langly, M. S, and Heel, R. C. *Drugs,* 1988, 35, 334-372. Propofol is only sparingly soluble in water and is currently marketed in a 10% soybean oil based lipid emulsion similar to formulations used for parenteral nutrition.

Propofol is a $GABA_A$ agonist that activates multiple $GABA_A$ receptor subtypes, which are ion channels that transport chlorine anions across cell membranes, in the central nervous system. Although propofol is achiral, racemic mixtures of a number of dialkyl phenols are known agonists of the $GABA_A$ receptor (James et al., *J. Med. Chem.* 23, 1350, 1980; Krasowski et al., *J. Pharmacol. & Exp. Therapeutics* 297, 338, 2001). James et al., report finding propofol to be superior in its overall profile to other analogues evaluated.

Propofol is preferred by many clinicians due to its excellent pharmacokinetic, pharmacodynamic, emergence and recovery profiles. However, undesired side-effects (e.g., respiratory depression, ICU syndrome, injection pain and hemodynamic effects) produced at or near the therapeutic dose greatly limit its utility in multiple clinical settings. Of particular concern are the hemodynamic effects. Administration of propofol, particularly in bolus form, often produces decreases in blood pressure without a compensatory increase in heart rate. A variety of clinical conditions are incompatible with the use of propofol because of undesired and potentially harmful hemodynamic consequences. Examples of such conditions include cardiovascular disease such as coronary artery disease, cardiomyopathy, ischemic heart disease, valvular heart disease, and congenital heart disease. Chronic hypertension, cerebrovascular disease, brain injury, and advanced age can make the use of propofol difficult or problematic because of its hemodynamic properties. Patients with acute blood loss, dehydration, or severe infection including those with hemorrhagic shock, hypovolemic shock, or septic shock may be exposed to excessive hazard were propofol employed. The hemodynamic properties of propofol may limit its use in patients receiving other medications or treatments such as spinal anesthesia, epidural anesthesia, or vasoactive medications.

SUMMARY OF THE INVENTION

The invention provides therapeutic compounds that demonstrate similar or improved pharmacological activity compared to propofol along with an improved hemodynamic profile.

Accordingly, in one embodiment the invention provides a (−)-stereoisomer of

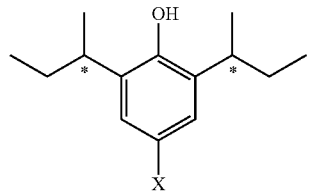

(I)

wherein X is H or F, or a salt or prodrug thereof.

The invention also provides a pharmaceutical composition comprising a (−)-stereoisomer of formula (I) or a pharmaceutically acceptable salt or prodrug thereof and a pharmaceutically acceptable carrier.

The invention also provides a method to treat nausea, vomiting, migraine, neurodegenerative conditions of the nervous system (e.g., Friedrich's disease, Parkinson's disease, Alzheimer's disease, Huntington's disease, amyotrophic lateral sclerosis (ALS), multiple sclerosis (MS), Pick disease, etc.), trauma to the central nervous system (e.g., skull fracture and its resulting edema, concussion, contusion, brain hemorrhages, shearing lesions, subdural and epidural hematoma, and spinal cord injury (e.g., mechanical injury due to compression or flexion of the spinal cord)), seizures (e.g., epileptic seizures) or a free radical associated disease (e.g., ischemic reperfusion injury, inflammatory diseases, systemic lupus erythematosis, myocardial infarction, stroke, traumatic hemorrhage, cataract formation, uveitis, emphysema, gastric ulcers, neoplasia, radiation sickness, etc.) in an animal comprising administering an effective amount of a (−)-stereoisomer of formula (I) or a pharmaceutically acceptable salt or prodrug thereof to the animal.

The invention also provides a method for inducing or maintaining general anesthesia in an animal comprising administering an effective amount of a (−)-stereoisomer of formula (I) or a pharmaceutically acceptable salt or prodrug thereof to the animal.

The invention also provides a method for promoting sedation in an animal comprising administering an effective amount of a (−)-stereoisomer of formula (I) or a pharmaceutically acceptable salt or prodrug thereof to the animal.

The invention also provides a method for treating a migraine in an animal comprising administering an effective amount of a (−)-stereoisomer of formula (I) or a pharmaceutically acceptable salt or prodrug thereof to the animal.

The invention also provides a method for treating insomnia in an animal comprising administering an effective amount of a (−)-stereoisomer of formula (I) or a pharmaceutically acceptable salt or prodrug thereof to the animal.

The invention also provides a method for promoting an anxiolytic effect in an animal comprising administering an effective amount of a (−)-stereoisomer of formula (I) or a pharmaceutically acceptable salt or prodrug thereof to the animal.

The invention also provides a method for treating addiction withdrawal in an animal comprising administering an effective amount of a (−)-stereoisomer of formula (I) or a pharmaceutically acceptable salt or prodrug thereof to the animal.

The invention also provides a method for promoting an antiemetic effect in an animal comprising administering an effective amount of a (−)-stereoisomer of formula (I) or a pharmaceutically acceptable salt or prodrug thereof to the animal.

The invention also provides a method for agonizing a GABA receptor comprising contacting the receptor (in vitro or in vivo) with an effective amount of a (−)-stereoisomer of formula (I) or a pharmaceutically acceptable salt thereof.

The invention also provides a method for agonizing a GABA receptor in an animal comprising administering an effective amount of a (−)-stereoisomer of formula (I) or a pharmaceutically acceptable salt or prodrug thereof to the animal.

The invention also provides a (−)-stereoisomer of formula (I) or a pharmaceutically acceptable salt or prodrug thereof for use in medical therapy.

The invention also provides the use of a (−)-stereoisomer of formula (I) or a pharmaceutically acceptable salt or prodrug thereof to prepare a medicament for treating nausea, vomiting, migraine, neurodegenerative conditions of the nervous system (e.g., Friedrich's disease, Parkinson's disease, Alzheimer's disease, Huntington's disease, amyotrophic lateral sclerosis (ALS), multiple sclerosis (MS), Pick disease, etc.), trauma to the central nervous system (e.g., skull fracture and its resulting edema, concussion, contusion, brain hemorrhages, shearing lesions, subdural and epidural hematoma, and spinal cord injury (e.g., mechanical injury due to compression or flexion of the spinal cord)), seizures (e.g., epileptic seizures) or a free radical associated disease (e.g., ischemic reperfusion injury, inflammatory diseases, systemic lupus erythematosis, myocardial infarction, stroke, traumatic hemorrhage, cataract formation, uveitis, emphysema, gastric ulcers, neoplasia, radiation sickness, etc.) in an animal.

The invention also provides the use of a (−)-stereoisomer of formula (I) or a pharmaceutically acceptable salt or prodrug thereof to prepare a medicament for inducing or maintaining general anesthesia in an animal.

The invention also provides the use of a (−)-stereoisomer of formula (I) or a pharmaceutically acceptable salt or prodrug thereof to prepare a medicament for promoting sedation in an animal.

The invention also provides the use of a (−)-stereoisomer of formula (I) or a pharmaceutically acceptable salt or prodrug thereof to prepare a medicament for treating a migraine in an animal.

The invention also provides the use of a (−)-stereoisomer of formula (I) or a pharmaceutically acceptable salt or prodrug thereof to prepare a medicament for treating insomnia in an animal.

The invention also provides the use of a (−)-stereoisomer of formula (I) or a pharmaceutically acceptable salt or prodrug thereof to prepare a medicament for promoting an anxiolytic effect in an animal.

The invention also provides the use of a (−)-stereoisomer of formula (I) or a pharmaceutically acceptable salt or prodrug thereof to prepare a medicament for treating addiction withdrawal in an animal.

The invention also provides the use of a (−)-stereoisomer of formula (I) or a pharmaceutically acceptable salt or prodrug thereof to prepare a medicament for promoting an antiemetic effect in an animal.

The invention also provides the use of a (−)-stereoisomer of formula (I) or a pharmaceutically acceptable salt or prodrug thereof to prepare a medicament for agonizing a GABA receptor in an animal.

The invention also provides synthetic processes and intermediates disclosed herein that are useful for preparing a (−)-stereoisomer of formula (I) or a salt or prodrug thereof.

DETAILED DESCRIPTION OF THE INVENTION

Figure 1:
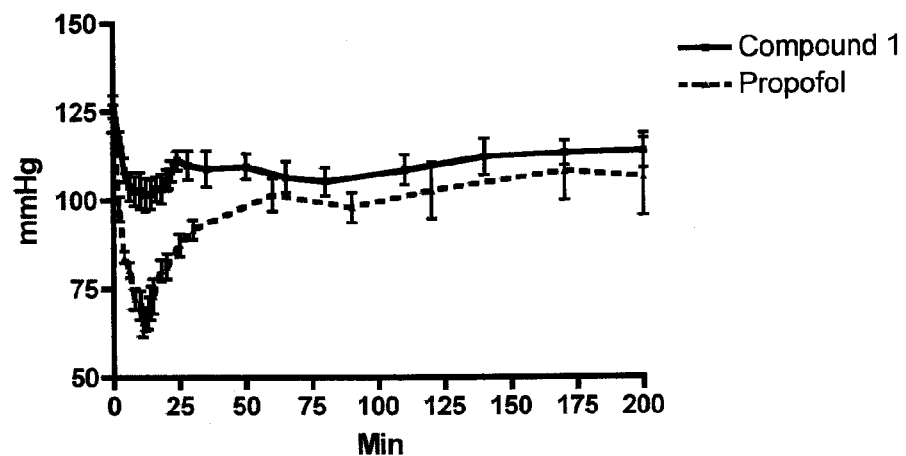
FIG. 1 shows the effect on mean arterial blood pressure (mm Hg) in pigs following IV infusion of the (−) stereoisomer of formula (I) in which X is H in comparison with propofol.

The present invention provides a (−) stereoisomer of formula (I), or a salt or prodrug thereof as defined hereinabove.

The absolute configuration of such a stereoisomer has been determined to be (R,R).

In one embodiment, X is H. When X is H, the stereoisomer may also be referred to by the name (R,R)-2,6-di-sec-butylphenol.

Compared with propofol, (R,R)-2,6-di-sec-butylphenol has been found to demonstrate a surprisingly improved overall profile of activity as an anesthetic. More particularly, the compound has been found to produce a more potent effect on anesthetic activity, to exhibit a higher therapeutic index and to retain a comparable pharmacokinetic profile, e.g., exhibit a similar clearance rate. The compound also can produce a less potent effect on mean arterial pressure, heart rate and/or cardiac output. Furthermore, it is believed that clinical trials will demonstrate that the compound causes less pain on injection than propofol. Injection pain associated with propofol has been correlated to the concentration of propofol in the aqueous phase of its lipid emulsion vehicle. When formulated in identical lipid emulsions, the aqueous phase concentration of (R,R)-2,6-di-sec-butylphenol has been found to be significantly reduced (by more than 90%) compared to propofol.

The other two isomers of 2,6-di-sec-butylphenol, the (S,S) or (+) and (meso) stereoisomers have also been found, unexpectedly, to demonstrate improved hemodynamic profiles along with similar or improved pharmacological activities, compared to propofol. However, the improved overall profile of activity as an anesthetic of (R,R)-2,6-di-sec-butylphenol has been found to be unique to this isomer of this dialkylphenol.

Accordingly, compounds according to the invention are particularly useful for inducing or maintaining general anesthesia or promoting sedation in a patient. They are particularly useful for anesthetizing patients having an elevated susceptibility to hemodynamic effects. Such patients include patients suffering from cardiovascular disease such as coronary artery disease, cardiomyopathy, ischemic heart disease, valvular heart disease, and congenital heart disease; patients suffering from chronic hypertension, cerebrovascular disease, or brain injury; patients of an advanced age (for example over 50, 60, 70 or 80 years old); patients with acute blood loss, dehydration, or severe infection including those with hemorrhagic shock, hypovolemic shock, or septic shock; and patients receiving spinal anesthesia, epidural anesthesia, or vasoactive medications; see e.g., Reich D L et al, 2005. Anesth Analg 101, 622. For example, the patient may be one for whom the American Society of Anesthesiologists (ASA) physical status is at least 3. The present invention also contemplates administering compounds according to the invention to patients that have not been pre-medicated for pain on injection.

As used herein, the term "Pharmaceutically acceptable carrier" includes diluents, adjuvants, excipients or vehicles.

The term "Animal" includes mammals such as, for example, humans, companion animals, zoo animals and livestock.

The term "Treating" a disease or disorder includes 1) ameliorating the disease or disorder (i.e., arresting or reducing the development of the disease or disorder or at least one of the clinical symptoms thereof), 2) ameliorating at least one physical parameter, which may not be discernible by the patient, 3) inhibiting the disease or disorder which can be either physically, (e.g., stabilization of a discernible symptom), physiologically, (e.g., stabilization of a physical parameter) or both, or 4) delaying the onset of the disease or disorder.

Stereoisomeric purity of compounds and prodrugs described herein may be established by conventional analytical methods well known to those of skill in the art. For example, use of chiral NMR shift reagents, gas chromatographic analysis using chiral columns, high pressure liquid chromatographic analysis using chiral columns, polarimetry, isotopic dilution, calorimetry, enzymatic methods, capillary electrophoresis on chiral gels, formation of diastereomeric derivatives through reaction with chiral reagents and conventional analysis via established analytical methods may be used to establish the stereochemical purity of a specific stereoisomer. Alternatively, synthesis using starting materials of known stereochemical enrichment may be used to establish the stereochemical purity of the compounds described herein. Other analytical methods for demonstrating stereochemical homogeneity are known in the field.

The present invention provides a stereoisomer of formula (I) or a salt or prodrug thereof in a non-racemic (i.e., an enantiomerically enriched) form at the centers marked by "*" in formula (I). Thus the invention includes a stereoisomer of formula (I) in an enriched mixture that contains no more than 45% of other enantiomers or diastereomers of that compound of formula (I) that is shown or its salt or prodrug. The (−)-enantiomer isolated in Example 1 below is a specific stereoisomer of the invention. In some embodiments of the invention, an enriched mixture contains no more than about 40%, 35%, 30%, 25%, 20%, 15%, 10%, 5%, 4%, 3%, 2%, or 1% of other enantiomers or diastereomers of a compound of formula (I) or its salt or prodrug. In another embodiment of the invention an enriched mixture contains less than about 1% of other enantiomers or diastereomers of a compound of formula (I) or its salt or prodrug.

Methods for Preparing a Compound of Formula (I)

Generally, compounds of formula (I) may be prepared by at least three different approaches. In one approach, a racemic and/or diastereomeric mixture is prepared using conventional methods of organic synthesis or purchased from commercial sources and the mixture resolved using methods known to those of skill in the art such as, for example, fractional crystallization, separation on chiral columns (See Example 1 below), formation of derivatives and separation or kinetic resolution thereof, etc. to provide substantially pure stereoisomers of formula (I) or stereoisomerically enriched mixtures of compounds of formula (I). Alternatively, asymmetric synthesis may be used to prepare compounds of formula (I). Known chiral precursors can be used to prepare substantially pure stereoisomers of formula (I) or stereoisomerically enriched mixtures of compounds of formula (I) using known methods. Other methods include preparation of chiral intermediates using, for example, enantioselective hydrogenation, enantioselective reduction, enantioselective carbon-carbon bond formation, enzymatic cleavage of racemic acetates, etc., followed by conversion to a compound of formula (I) using conventional methods of organic synthesis.

In one method, a stereoisomer of formula (I) can be prepared using a chiral isocyanate to form a mixture of carbamate diastereomers that can be separated to yield the desired diastereomer of formula (I) after hydrolysis of the carbamate residue.

According to another aspect, therefore, the present invention provides a process for preparing a (−) stereoisomer of formula (I) or a salt or prodrug thereof, which comprises hydrolysing a carbamic acid (−)-2,6-di-sec-butylphenyl ester diastereoisomer of formula

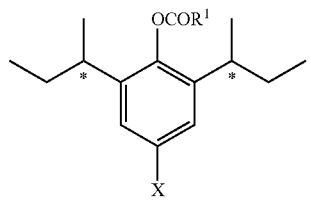

in which $R^1$ represents a chiral amino group, followed if required by forming the free phenol or a salt (such as a pharmaceutically acceptable salt) or pro-drug thereof.

The hydrolysis may be effected by reacting the carbamate with a base, for example an alkali metal hydroxide, such as potassium or sodium hydroxide, which affords a salt of the (−) stereoisomer of formula (I), such as an alkali metal salt. The free phenol may be obtained by treating this salt with an acid, such as hydrochloric acid. The chiral amino group may be, for example, a chiral 1-arylethylamino group, for example an (R)-1-arylethylamino group such as (R)-1-phenylethylamino.

The carbamate starting material may be prepared by reacting a racemic mixture of the corresponding 2,6-di-sec-butylphenol with a chiral isocyanate to afford a mixture of diastereoisomers comprising the carbamic acid (−)-2,6-di-sec-butylphenyl ester diastereoisomer; and separating the corresponding carbamic acid (−)-2,6-di-sec-butylphenyl ester diastereoisomer of formula (II).

The chiral isocyanate may be, for example, a chiral 1-arylethylisocyanate, for example an (R)-1-arylethylisocyanate such as (R)-(+)-1-phenylethylisocyanate. The resultant product is a mixture of the corresponding 1-arylethylcarbamic acid 2-sec-butyl-6-isopropylphenyl ester diastereoisomers. The desired diastereoisomer can be separated by chromatography using, for example, silica as the stationary phase, or by crystallization.

It has been found, surprisingly, that the use of R-(+)-1-phenylethylisocyanate in the above-described method provides an exceptionally good separation of the stereoisomers of 2,6-di-sec-butylphenol, compared with the use of other chiral acylating or sulfonating reagents, such as chiral carboxylic acids or chiral sulfonic acids.

Processes for preparing a stereoisomer of formula (I) or a salt thereof are provided as further embodiments of the invention.

Salts

In cases where compounds are sufficiently acidic, a salt of a compound of formula (I) can be useful as an intermediate for isolating or purifying a compound of formula (I) or an enriched mixture thereof. Additionally, administration of a compound of formula (I) as a pharmaceutically acceptable salt may be appropriate. Examples of pharmaceutically acceptable salts include salts that are obtained using standard procedures well known in the art, for example by reacting a sufficiently acidic compound of formula (I) with a suitable base affording a physiologically acceptable cation. For example, alkali metal (for example, sodium, potassium or lithium) or alkaline earth metal (for example calcium) salts can be made.

Pharmaceutical Compositions

The pharmaceutical compositions disclosed herein comprise a compound of formula (I) disclosed herein with a suitable amount of a pharmaceutically acceptable carrier, so as to provide a form for proper administration to a patient. The compounds of formula (I) may be formulated as pharmaceutical compositions and administered to a patient, in a variety of forms adapted to the chosen route of administration, e.g., orally, parenterally, intravenously, intramuscularly, topically or subcutaneously.

Thus, the compounds of formula (I) can be systemically administered, in combination with pharmaceutically acceptable carriers such as inert diluents or edible carriers. Such compositions and preparations may contain at least 0.1% of active compound. The percentage of the compositions and preparations can, of course, be varied and can conveniently be between about 0.1% to about 60% of the weight of a given unit dosage form. The amount of active compound in such therapeutically useful compositions is such that an effective dosage level is obtained.

The compounds of formula (I) described herein are typically formulated as pharmaceutical compositions suitable for intravenous administration. The compounds of formula (I) may be relatively insoluble in water. Thus, for intravenous administration, the compounds of formula (I) are typically formulated in aqueous media using one or more water-immiscible solvents and one or more emulsifiers or surfactants. Individual formulations can include one or more additional components such as stabilizers, tonicity modifiers, bases or acids to adjust pH and solubilizers. The formulations may also optionally contain a preservative, such as, for example, ethylenediaminetetraacetic acid (EDTA) or sodium metabisulfite. Useful oil-in-water emulsions that contain a preservative such as EDTA that may be used in conjunction with compounds described herein are described in U.S. Pat. Nos. 5,908,869, 5,714,520, 5,731,356 and 5,731,355.

A wide range of water-immiscible solvents can be used in the pharmaceutical compositions described herein. The water-immiscible solvent can be a vegetable oil, such as, for example, soybean, safflower, cottonseed, corn, sunflower, arachis, castor or olive oil. Alternatively, the water-immiscible solvent may be an ester of a medium or long-chain fatty acid, such as, for example, a mono-, di-, or triglyceride, an ester of a combination of a medium and long-chain fatty acid or a chemically modified or manufactured material such as ethyl oleate, isopropyl myristate, isopropyl palmitate, a glycerol ester, polyoxyl or hydrogenated castor oil. The water-immiscible solvent can also be a marine oil, such as, for example cod liver or another fish-derived oil. Other suitable solvents include fractionated oils, such as, for example, fractionated coconut oil or modified soy bean oil. The water-immiscible solvent may include "structured lipids." (see, e.g., Lipid Biotechnology, T. M. Kuo and H. W. Gardner (eds.), Marcel Dekker, Inc. New York, N.Y.). Many structured lipids are available from commercial suppliers such as Danisco A/S, Copenhagen Denmark and S&J Lipids, Ostrander, Ohio.

The pharmaceutical compositions described herein can also contain an emulsifier. Suitable emulsifiers include synthetic non-ionic emulsifiers, such as, for example, ethoxylated ethers, ethoxylated esters, polyoxypropylene-polyoxyethylene block co-polymers and phospholipids. Naturally-occurring phospholipids, such as egg or soya phospholipids, and modified or artificially manipulated phospholipids or mixtures thereof can also be used. In some embodiments, emulsifiers are egg phospholipids and soya phospholipids. Egg yolk phospholipids include phosphatidylcholine, lecithin and phosphatidylethanolamine.

The pharmaceutical formulations described herein can comprise a lipid emulsion comprising from about 0.1% to about 5% (w/w) of a formula (I) compound, from about 5 to about 25% (w/w) water immiscible solvent and from about 40% to about 90% (w/w) water. A preferred formulation comprises from about 0.5% to about 2% (w/w) of a formula (I) compound. In one embodiment, a pharmaceutical formulation comprises from about 0.5% to about 5% (w/w) of a formula (I) compound and from about 0% to about 50% (w/w) of a water immiscible solvent.

The pharmaceutical formulations described herein may also include stabilizing agents. Anionic stabilizers include, for example, phosphatidylethanolamines, conjugated with polyethylene glycol, (PEG-PE) and phosphatidylglycerols, a specific example of which is dimyristolphosphatidylgylcerol (DMPG). Additional stabilizers include, but are not limited to, oleic acid and its sodium salt, cholic acid and deoxycholic acid and respective salts thereof, cationic lipids such as stearylamine and oleylamine, and 3l3-[N-(N',N'-dimethylaminoethane)carbamoyl]cholesterol (DC-Chol).

The pharmaceutical compositions described herein can be made isotonic with blood by the incorporation of a suitable tonicity modifier. Glycerol is most frequently used as a tonicity modifier. Alternative tonicity modifying agents include xylitol, mannitol and sorbitol. The pharmaceutical compositions are typically formulated to be at physiologically neutral pH, typically in the range 6.0-8.5. The pH can be adjusted by the addition of base, for example, NaOH or $NaHCO_3$, or in some cases acid, such as HCl.

The compounds of formula (I) can be formulated with pharmaceutically safe oil-water emulsions comprising a vegetable oil, a phosphatide emulsifier, typically egg lecithin or soybean lecithin, and a tonicity modifier such as, for example. Liposyn® II and Liposyn® III (Abbott Laboratories, North Chicago. IL) and Intralipid® (Fresenius Kabi AB, Uppsala, Sweden) or other similar oil-water emulsions.

Compounds of formula (I) can also be formulated in a triglyceride comprising esters of at least one medium chain length ($C_6$-$C_{12}$) fatty acid. In some embodiments, the triglyceride is an ester of a $C_8$-$C_{10}$ fatty acid. Triglycerides suitable for formulating compounds of formula (I) include, but are not limited to, Miglyol® (Condea Chemie GmbH (Witten, Germany). For example, Miglyol® 810 or 812 (caprylic ($C_{10}$)/capric ($C_8$) glyceride) is useful for formulation of compounds of formula (I).

Additionally, compounds of formula (I) described herein can be formulated analogously to pharmaceutical compositions of propofol as described, for example, in U.S. Pat. Nos. 4,056,635, 4,452,817 and 4,798,846.

Still other suitable formulations for use in the present invention can be found, for example in Remington's Pharmaceutical Sciences, Philadelphia, Pa., 19th ed. (1995).

Therapeutic/Prophylactic Administration And Doses

A compound of formula (I) and/or pharmaceutical compositions thereof may be administered alone or in combination with other pharmaceutical agents including compounds disclosed herein and/or pharmaceutical compositions thereof. The compounds disclosed herein may be administered or applied per se or as pharmaceutical compositions. The specific pharmaceutical composition depends on the desired mode of administration, as is well known to the skilled artisan.

Compounds disclosed herein and/or pharmaceutical compositions thereof may be administered to a subject by intravenous bolus injection, continuous intravenous infusion, oral tablet, oral capsule, oral solution, intramuscular injection, subcutaneous injection, transdermal absorption, buccal absorption, intranasal absorption, inhalation, sublingually, intracerebrally, intravaginally, rectally, topically, particularly to the ears, nose, eyes, or skin or any other convenient method known to those of skill in the art. In some embodiments, compounds disclosed herein and/or pharmaceutical compositions thereof are delivered via sustained release dosage forms, including oral sustained release dosage forms. Administration can be systemic or local. Various delivery systems are known, (e.g., encapsulation in liposomes, microparticles, microcapsules, capsules, "patient controlled analgesia" drug delivery systems, etc.) that can be used to deliver compounds disclosed herein and/or pharmaceutical compositions thereof.

The amount of compounds disclosed herein and/or pharmaceutical compositions thereof that will be effective can be determined by standard clinical techniques known in the art. The amount of compounds disclosed herein and/or pharmaceutical compositions thereof administered will, of course, be dependent on, among other factors, the subject being treated, the weight of the subject, the age of the subject, the condition of the subject, the intended effect of the compounds, the manner of administration and the judgment of the prescribing physician. For example, the dosage level of a (R,R) or (−) stereoisomer of formula (I) for producing general anesthesia may be in the range of from about 1 to about 10 mg/kg. Preferred induction doses range from about 1 to about 2.5 mg/kg. Preferred maintenance doses range from about 1 to about 15 mg/kg/hr. Preferred doses to produce a sedative effect range from about 0.3 to about 6 mg/kg/hr.

Combination Therapy

In certain embodiments, compounds disclosed herein and/or pharmaceutical compositions thereof can be used in combination therapy with at least one other therapeutic agent. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent such as, for example, other sedative hypnotic agents (e.g., etomidate, thiopental, midazolam, dexmedetomidine, ketamine), anesthetic agents (e.g., desflurane, sevoflurane, isoflurane, nitrous oxide), analgesics (e.g., an opioid such as remifentanil, morphine, meperidine, hydromorphone, methadone, fentanyl, sulfentanil, or alfentanil, or a non-opioid analgesic such as ketorolac, gapapentin, lidocaine, or ketamine), paralytic agents, such as rocuronium, cis-atracurium, vecuronium, or pancuronium bromide, anti-emetics (e.g., ondansetron, dolasetron, droperidol), cardiovascular agents (e.g., metoprolol, propranolol, esmolol, clonidine, phenylephrine, ephedrine, epinephrine, norepineprine, dopamine, diltiazem, atropine, glycopyrrolate, lisinopril, nitroglycerin, sodium nitroprusside, digoxin, milrinone), steroids (e.g. dexamethasone, hydrocortosone, methylprednisolone), anti-infective agents (e.g., cefazolin, vancomycin), diuretics (e.g., furosemide, hydrochlorothiazide, spironolactone), mood altering medications (e.g., fluoxetine, aripiprazole), or stimulants such as nicotine or cytisine.

For example, compounds disclosed herein and/or pharmaceutical compositions thereof may be administered together with other therapeutic agents. In other embodiments, compounds disclosed herein and/or pharmaceutical compositions thereof are administered prior or subsequent to administration of other therapeutic agents.

Prodrugs

The term "prodrug" as used herein refers to a compound that can be metabolized or converted in vivo to provide a compound of formula (I). Typically, prodrugs include compounds that are prepared by modifying the phenol group in a compound of formula (I) to provide a corresponding compound that can be metabolized or converted in vivo to provide the corresponding compound of formula (I). Prodrugs of phenolic compounds as well as methods for their preparation have been reported. For example, see U.S. Patent Application Publication Numbers 20070015716, 20060287525, 20060205969, 20060041011, 20050239725, and 20050107385.

Other suitable prodrug groups are discussed in the following Published International Patent Applications and Published US Patent Applications: WO 2005023204; US 2005107385; US 2005004381; WO 2004092187; WO 2004032971; US 2006100163; WO2006033911; WO 2004033424; US 2005267169; WO2003086413; US 2002370213; WO 2003057153; US 2001342755; US 2002099013; WO 2002034237; US 2004127397; WO 2002013810; WO 2000048572; US 2006166903; WO 200008033; US 2001025035; WO 9958555; and US 199875356; and in the other following publications: Krasowski, M. D. Current Opinion in Investigational Drugs (Thompson Scientific) (2005) 6(1), 90-98; Fechner, J. et al., *Anesthesiology,* 2004. 101. 3. 626-639; Altomare C. et al., *European Journal of Pharmaceutical Sciences;* 2003, 20, 1, 17-26; Sagara, Y. et al., *Journal of Neurochemistry:* 1999; 73, 6, 2524-2530, and Trapani, G., et al., *International Journal of Pharmaceuticals,* 1998, 175, 2, 195-204.

As described hereinabove, the other two isomers of 2,6-di-sec-butylphenol, the (S,S) or (+) and (meso) isomers of formula (I), have also been found to demonstrate an improved hemodynamic profile along with a similar or improved pharmacological activity, compared to propofol. Accordingly, the present invention also provides each of these isomers, their para-fluoro derivatives and pharmaceutically acceptable salts and pro-drugs thereof, and pharmaceutical compositions thereof, for use as anesthetics.

The (S,S) or (+) and (meso) stereoisomers of formula (I), their salts and prodrugs thereof may each be prepared following the general methods described for the preparation of the corresponding (R,R) or (−) stereoisomers. For example, the stereoisomers may be separated from the racemic compound by chiral phase chromatography, for example as described in Example 2 herein. It has been found that the (S,S) or (+) stereoisomer of 2,6-di-sec-butylphenol may advantageously be prepared by reacting a racemic mixture of the corresponding 2,6-di-sec-butylphenol with an acyl halide (for example an aroyl halide such as benzoyl chloride) to afford a mixture of carbonate diastereomers that can be separated to yield the desired diastereomer of formula (I) after hydrolysis of the carbonate residue. An example of such a process is described in Example 5a hereinafter.

The (S,S) or (+) and (meso) stereoisomers of formula (I) may exist, be formulated and be administered to patients as described and exemplified herein for the (R,R) or (−) stereoisomers. For the (S,S) or (+) stereoisomers, the dosage level for producing general anesthesia may be in the range of from about 1 to about 12 mg/kg. Preferred induction doses range from about 1.2 to about 4 mg/kg. Preferred maintenance doses range from about 1.5 to about 30 mg/kg/hr. Preferred doses to produce a sedative effect range from about 0.5 to about 12 mg/kg/hr. For the (meso) stereoisomers, the dosage level for producing general anesthesia may be in the range of from about 1 to about 10 mg/kg. Preferred induction doses range from about 1 to about 3 mg/kg. Preferred maintenance doses range from about 1 to about 20 mg/kg/hr. Preferred doses to produce a sedative effect range from about 0.3 to about 8 mg/kg/hr.

The ability of a compound of the invention to produce a sedative or hypnotic effect can be determined using standard pharmacological models which are well known to the art. The hemodynamic profile of a compound of the invention can be determined using standard pharmacological models which are well known to the art.

The invention will now be illustrated by the following non-limiting Examples.

EXAMPLE 1

Isolation of Stereoisomer of a Compound of Formula (I) Via HPLC Separation of Diasteriomeric Carbamates of 2,6-Di-Sec-Butylphenol

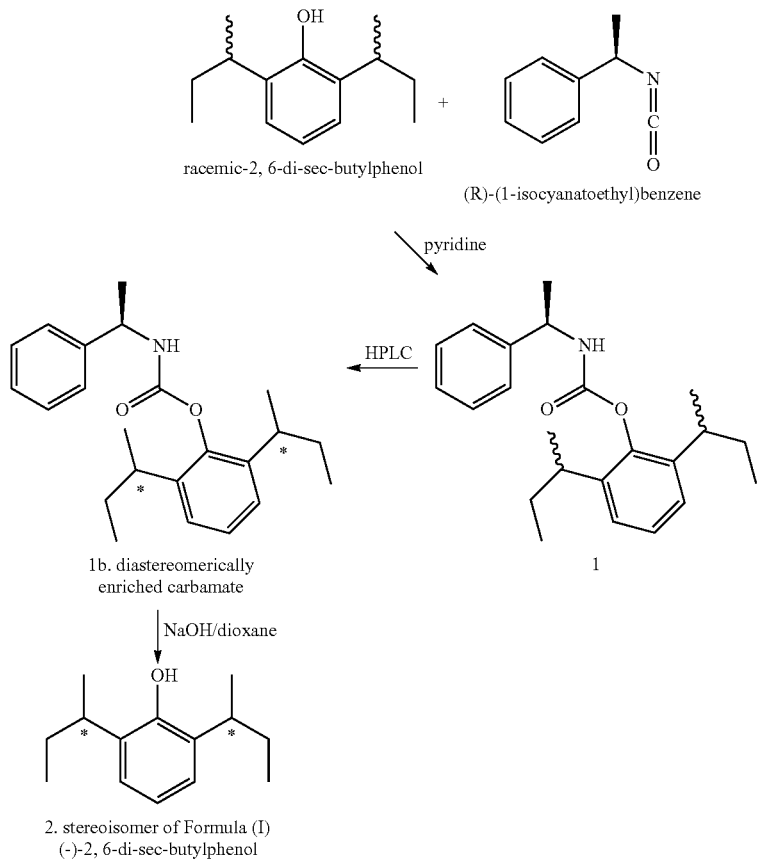

1b. diastereomerically enriched carbamate 2. stereoisomer of Formula (I) (-)-2, 6-di-sec-butylphenol Synthesis of R-(+)-1-Phenyl-ethyl)-carbamic acid 2,6-di-sec-butylphenyl ester (1): A mixture of 2,6-di-sec-butylphenol (2.06 g, 10 mmol), R-(+) 1-phenylethylisocyanate (1.47 g, 10 mmol), and 4-(dimethylamino)pyridine (0.06 g, 0.5 mmol) was heated at 100° C. in 10 ml dry pyridine overnight. The reaction mixture was evaporated, and the resulting residue was treated with ethyl acetate (75 ml) and 1M HCl aq (100 ml). The organic layer was washed twice with 1M HCl aq (2×100 mL), brine (100 ml) and dried over anhydrous MgSO$_4$. Evaporation of the solvent provided carbamate (1) (3 g, 85%).

Separation of diastereomers of R-(+)-1-Phenyl-ethyl)-carbamic acid 2,6-di-sec-butylphenyl ester (1b): HPLC separation was performed on HPLC silica gel column (250×41.5 mm), sorbent Si-60A 10 mm. Gradient: hexanes-ethyl acetate 0-10% in 72 min; flow rate 50 ml/min; loading 1 g of (1) in 10 ml hexane. The fraction with the desired isomer of the carbamate (1b) were collected and evaporated (0.18 g, 72%).

Analysis of optical purity by chiral chromatography: Analyses 2,6-di-sec-butylphenols were performed on CHIRALCEL OD-H column (4.6×250 mm) in isocratic mode, mobile phase -n-hexanes, flow rate 1 ml/min, 20 min, detection 270 nm. Samples were dissolved in hexanes. Carbamates were preliminary hydrolyzed to 2,6-di-sec-butylphenols at 100° C. for 1-2 min. in a 1:1 mixture dioxane: 1M NaOH aq. 2,6-Di-sec-butylphenols were extracted with ether. The ether layer was evaporated, and the residual oil was dissolved in n-hexanes.

Synthesis of (−)-2,6-di-sec-butylphenol (2): R-(+)-1-Phenyl-ethyl)-carbamic acid (−)-2,6-di-sec-butylphenyl ester (1b) (4.1 g, 11.6 mmol) was dissolved in a 100 ml 1:1 mixture of dioxane: 1M NaOH aq. The reaction mixture was stirred at 70° C. for 15 min. Volatiles were removed at reduced pressure to a volume of ~50-70 ml. The pH was adjusted to 3-4 with 1M HCl. The phenol was extracted with ether (3×50 ml), washed with 1 M HCl, brine and dried over anhydrous MgSO$_4$. Evaporation yielded crude yellow oil (2.4 g, ~100%). Vacuum distillation was performed (120-125° C./~5 mm) (2.1 g, 89%). Optical rotation: $\alpha^{20}_D$=−14.11° (c=2, pentane).

EXAMPLE 2

Direct separation of stereoisomers of 2,6-di-sec-butylphenol

Separation of the mixture of stereoisomers of 2,6-di-sec-butylphenol was achieved by chiral HPLC. 2,6-Di-sec-butylphenol (1 mg/ml in HPLC grade n-hexane) was injected onto a chiral HPLC column (Daicel, Inc., CHIRALCEL OD-H 20×250 mm, 5 um). Separation was achieved using an isocratic gradient using HPLC grade n-hexane as the mobile phase at a flow rate of 10 ml/minute at ambient temperature.

Peak detection was at 270 mm. 2,6-Di-sec-butylphenol showed three peaks in a 1:2:1 ratio corresponding to enantiomer 1 (the desired stereoisomer), (meso)-2,6-di-sec-butylphenol, and enantiomer 2. The isolated enantiomer 1 (1 mg/ml) was dissolved in HPLC grade n-hexane and injected onto a chiral HPLC column (Daicel, Inc., CHIRALCEL OD-H 4.6×250 mm, 5 um), run with an isocratic gradient using HPLC grade n-hexane as the mobile phase at a flow rate of 0.7 ml/minute at ambient temperature. Peak detection was at 270 mm., and showed a retention time of 17.1 minutes, and a purity of >%99 of the isomer. Optical rotation: $\alpha^{20}{}_D=-11.91°$. Following the same analytical procedure as for enantiomer 1, enantiomer 2 showed a retention time of 19.6 minutes, and a purity of >%95 of the isomer, and (meso)-2,6-di-sec-butylphenol showed a retention time of 18.8 minutes, and a purity of >%96 of the isomer.

EXAMPLE 3

Formulation

The following illustrates a representative dosage form containing a compound of formula (I) for therapeutic use.

| Ingredient | Batch Weight | w/w % |
|---|---|---|
| Soybean Oil | 70 g | 11.71 |
| Soybean Phospholipids (Lipid S-75) | 8.4 g | 1.41 |
| Compound of formula (I) | 3.5 g | 0.59 |
| Glycerine | 15.75 g | 2.64 |
| Disodium Edetate | 0.035 g | 0.01 |
| Sodium Hydroxide (pH adjustment) | | |
| Subtotal | 97.685 | |
| Sterile Water For Injection | 500 ml | 83.66 |
| Total | 597.685 | 100 |

EXAMPLE 4

Formulation

The following illustrates a representative dosage form containing a compound of formula (I) for therapeutic use.

| Ingredient | Batch Weight | w/w % |
|---|---|---|
| Soybean Oil | 70 g | 11.66 |
| Soybean Phospholipids (Lipid S-75) | 8.4 g | 1.40 |
| Compound of formula (I) | 6.0 g | 1.00 |
| Glycerine | 15.75 g | 2.62 |
| Disodium Edetate | 0.035 g | 0.01 |
| Sodium Hydroxide (pH adjustment) | | |
| Subtotal | 100.185 | |
| Sterile Water For Injection | 500 ml | 83.31 |
| Total | 600.185 | 100 |

EXAMPLE 5

Preparation of (R,R)-Di-sec-butylphenol using Chromatography to Separate Carbamate Diastereoisomers a) (R)-(+)-1-Phenyl-ethyl)-carbamic acid-2,6-di-sec-butylphenyl ester

Di-sec-butylphenol (available from Acros & AK Scientific) (5 grams (g). 21.1 millimoles (mmol)) was azeotropically dried on a rotavap (55° C., 48 torr) using 5 milliliters (ml or mL) of toluene and then charged into a 100-ml three-necked flask equipped with a magnetic stirrer, a reflux condenser, a thermocouple and a nitrogen ($N_2$) inlet. Toluene (10 ml) and 4-dimethylaminopyridine (0.085 g, 0.7 mmol) were added. (R)-(+)-1-phenylethyl isocyanate (3.5 g, 3.65 ml, 23.63 mmol) was introduced last. The resulting clear yellow mixture was heated under $N_2$ at 90° C. using a heating mantle and continued to stir at this temperature while monitoring the progress of the reaction by high pressure liquid chromatography (HPLC). After the reaction was finished (18-24 hours (h)) as judged by HPLC, the reaction mixture was concentrated on a rotavap (50-55° C./45-50 torr) to obtain a semi-solid (~9.4 g) which was dissolved in hot 2-propanol (18 ml). The solution was allowed to reach ambient temperature, seeded with pure (R)-(+)-1-Phenyl-ethyl)-carbamic acid-2,6-di-sec-butylphenyl ester, and placed in a refrigerator (4° C.) for 24-36 h for slow crystallization to occur. The precipitated yellow solids were filtered cold and dried on the filter funnel for 1-2 h. The first crop of product weighed 2.8 g (37.5% yield) and was found to be greater than (>) 95 area percent (A %) pure by HPLC analysis. The mother liquor was concentrated on a rotavap to ~⅔ of the original volume (distilled off 4 ml of 2-propanol), and then cooled to 0-5° C. for 6-8 h. The second crop of product was filtered cold, dried on the filter funnel to give an additional 2.6 g (34.9% yield) of product which was found to be ~88 A % by HPLC.

b) (R,R,R)-1-phenylethylcarbamic acid-2,6-di-sec-butylphenyl ester

To an Agilent HPLC system fitted with a diode array detector and a 0.46 cm ID×25 cm long 10 mm KROMASIL Silica Column was charged 714 mg of racemic R-(+)-1-phenyl-ethyl)-carbamic acid-2,6-di-sec-butylphenyl ester dissolved in 10 ml of hexane/ethyl acetate (98:2) to give a 71.4 g/l feed solution. The sample was eluted with hexane/ethyl acetate (98:2) at 2 ml/min at 25° C. Fractions containing (R,R,R)-1-phenylethylcarbamic acid-2,6-di-sec-butylphenyl ester were collected and evaporated under reduced pressure at <55° C. At the highest loading, the (R,R,R)-stereoisomer was collected with a chiral purity of 98.7% diastereomeric excess (de) and a total yield of 53%.

c) (R,R)-Di-sec-butylphenol

To a 100-ml three-necked flask equipped with a magnetic stirrer, a reflux condenser, a thermocouple and an $N_2$ inlet, was added tetrahydrofuran (THF) (9 ml), (R,R,R)-1-phenylethylcarbamic acid-2,6-di-sec-butylphenyl ester (1 g, 2.8 mmol), and 1.0 M sodium hydroxide (11.4 ml, 11.4 mmol). The resulting clear mixture was heated under $N_2$ at 55-60° C. using a heating mantle and continued to stir at this temperature while monitoring the progress of the reaction by HPLC. After the reaction was finished (6-8 h) as judged by HPLC, the reaction mixture was cooled to 15° C. and filtered to remove precipitated urea. The filtered cake was washed with cold THF (5 ml). The filtrate and the wash were combined, acidified to pH 2-3 with 3.0 M hydrochloric acid (HCl) (3.5 ml). After stirring for 10 minutes (min), ether (10 ml) was added and then resulting mixture was vigorously stirred for 15 min after which layers were separated. The organic layer was washed with 3.0 M HCl (3 ml), brine (5 ml), dried magnesium sulfate ($MgSO_4$), filtered to remove the drying agent, and then concentrated on a rotavap to give a semi solid yellow residue which was stirred with methyl tertiary butyl ether (MTBE) (3 ml) for 15 min and then filtered. The filtered cake was washed with MTBE (2 ml). The filtrate and the wash were combined, and then concentrated on a rotavap to give the title compound as a yellow oil (0.6 g, 100% crude yield) that was found to be greater than 93 A % pure by HPLC. The NMR (DMSO-$d_6$) was found to be consistent with the structure.

EXAMPLE 5a

Preparation of (S,S)-di-sec-butylphenol using Chromatography to Separate Carbonate Diastereoisomers a) 2,6-di-sec-Butylphenol benzoyl ester Di-sec-butylphenol (available from Acros & AK Scientific) is dried on a rotavap (55° C., 48 torr) using toluene and then charged into a 100-milliliter (ml or mL) three-necked flask equipped with a magnetic stirrer, a reflux condenser, a thermocouple and a nitrogen ($N_2$) inlet. Toluene and 4-dimethylaminopyridine are added followed by benzoyl chloride. The resulting mixture is heated under $N_2$ at 90° C. using a heating mantle and continued to stir at this temperature while monitoring the progress of the reaction by high performance liquid chromatography (HPLC). After the reaction is finished as judged by HPLC, the reaction mixture is concentrated on a rotavap (50-55° C./45-50 torr) to obtain a semi-solid.

b) (S,S)-2,6-di-sec-butylphenol benzoyl ester

To an Agilent HPLC system fitted with a diode array detector and a 0.46 cm ID×25 cm long 10 mm KROMASIL Silica Column is charged 2,6-di-sec-butylphenol benzoyl ester dissolved in hexane/ethyl acetate (98:2) to give a feed solution. The sample is eluted with hexane/ethyl acetate (98:2) at 25° C. Fractions containing (S,S)-2,6-di-sec-butylphenol benzoyl ester are collected and evaporated under reduced pressure at <55° C. to give a thin oil.

c) (S,S)-Di-sec-butylphenol

To a 100-ml three-necked flask equipped with a magnetic stirrer, a reflux condenser, a thermocouple and an $N_2$ inlet, is added tetrahydrofuran (THF), (S,S)-2,6-di-sec-butylphenol benzoyl ester, and 1.0 M sodium hydroxide. The resulting mixture is heated under $N_2$ at 55-60° C. using a heating mantle and continued to stir at this temperature while monitoring the progress of the reaction by HPLC. After the reaction is finished as judged by HPLC, the reaction mixture is cooled to 15° C. and filtered to remove precipitated urea. The filtered cake is washed with cold THF. The filtrate and the wash are combined, acidified to pH 2-3 with 3.0 M hydrochloric acid (HCl). After stirring for 10 min. ether is added and the resulting mixture is vigorously stirred for 15 min after which layers are separated. The organic layer is washed with 3.0 M HCl, brine, dried magnesium sulfate ($MgSO_4$), filtered to remove the drying agent, and then concentrated on a rotavap to give a residue which is stirred with methyl tertiary butyl ether (MTBE) for 15 min and then filtered. The filtered cake is washed with MTBE. The filtrate and the wash are combined, and then concentrated on a rotavap to give the title compound.

Biological Tests

The pharmacological profile of (R,R)-di-sec-butylphenol was evaluated in comparison with propofol in the tests described in the following Examples. In these Examples, (R,R)-di-sec-butylphenol is referred to as Compound 1.

EXAMPLE 6

Rat Hippocampal Brain Slice Assay

The abilities of Compound 1 and propofol to potentiate the action of agonists at the g-aminobutyric acid receptor subtype A ($GABA_A$ receptor) were tested and compared in a rat hippocampal brain slice electrophysiology assay.

Compound 1, prepared as described in Example 5, and propofol were each tested at five concentrations: 0.1, 1, 3, 10 and 30 micromolar (μM). Stock solutions of 100 millimolar (mM) propofol and of 100 mM Compound 1, each in DMSO, were diluted into saline to achieve the respective concentrations; 30 μM samples contained 0.03% DMSO; solutions containing up to 0.1% DMSO have no significant effect on the brain slice assay. EC50 and EC20 values were determined using a procedure similar to that described in Casasola et al. 2002, Epilepsy Research 47, 257, with modifications as set forth below.

Rat hippocampal slices were prepared as follows: Male Wistar rats (100-125 g) were anesthetized with isoflurane and decapitated, the brains quickly removed, collected, blocked, and cut using a vibratome (OTS-4000, Electron Microscope Sciences) into 400 micron (μm) transverse sections. Slices were transferred to a warmed (33° C.), submerged tissue-recording chamber perfused at 2.5-3 ml/min with modified artificial cerebrospinal fluid (120 mM sodium chloride. 3.5 mM, potassium chloride, 2.5 mM calcium chloride, 1.3 mM magnesium chloride, 1.25 mM sodium phosphate, 26 mM sodium carbonate, 10 mM glucose, saturated with 95% oxygen, pH 7.4). Hippocampal slices were equilibrated in the recording chamber for at least 1 hour.

Electrophysiology testing was accomplished as follows: A glass rod electrode (1-2 μM tip diameter) was filled with 3M sodium chloride (NaCl) and placed in the CA1 pyramidal cell layer of hippocampal slices. A 25 μM concentric bipolar stimulating electrode (SNE-100, Rhodes Medical Supply) was placed in the stratum radiatum of the CA1 area to stimulate the Schaffer collateral/commissural pathway. Population responses of the CA1 pyramidal cells were recorded with an Axoprobe-1A (Axon Instruments, Molecular Devices, Sunnyvale, Calif.). pCLAMP 8.2 (Axon Instruments) was used for acquiring the data, and Clampfit (Axon Instruments) was used for analysis. Stimulation consisted of a single square-wave pulse (0.3 millisecond (msec) duration) from the Grass S11 Stimulator (Grass Medical Instruments) and was delivered every 20 sec throughout the experimental period. The stimulus intensity was adjusted to evoke a response 80-90% of the maximum. Peak to peak amplitude of the population response from each stimulus was measured as an indicator of cell excitability.

Compound 1 and propofol, each in the presence of EC20 of muscimol (2 μM) were each sequentially perfused, starting from the lowest to the highest concentration, in the modified artificial cerebrospinal fluid of respective hippocampal slices. The effects of each concentration were measured from 4 to 7 min after Compound 1 or propofol application, respectively, at which time changes in the response were found to be stable. Muscimol (10 μM) was applied following the application of Compound 1 or propofol to verify the sensitivity of the preparation only if Compound 1 or propofol did not produce an adequate inhibition of the amplitude of the CA1 population spike (<90% inhibition). $GABA_A$ receptor channel antagonist picrotoxin (50 μM) was applied at the end of the recording to confirm that the response was mediated by $GABA_A$ receptor.

Data were acquired and analyzed using Clampfit and Excel (Microsoft), and reported as mean and individual values. The degree of population effect (%) was obtained by measuring the amplitude of the CA 1 population spike before (control) and after co-application of muscimol (EC20) and Compound 1 or propofol (the difference was normalized to control and multiplied by 100 to obtain the percent effect.

The data demonstrated that Compound 1 was a potent potentiator of the action of agonists at the $GABA_A$ receptor in the rat hippocampal brain slice, with an EC50 of 2.5 μM. Propofol had an EC50 of 4.8 μM. Thus Compound 1 behaved similarly to propofol in the hippocampal brain slice assay and fully potentiated the muscimol-mediated response at the $GABA_A$ receptor.

EXAMPLE 7

Target Specificity Studies

The abilities of Compound 1 and propofol to interact with a variety of biological targets were tested and compared.

Pharmacological profilings of Compound 1, prepared as described in Example 5, and propofol were performed by Cerep, Inc. (Redmond, Wash., USA) in their "Diversity Profile", a standard profile of 71 receptors (59 peptide, non-peptide, or nuclear receptors; 7 ion channels; 5 amine transporters) and 16 enzymes. Compound 1 and propofol were each tested at 10 μM, a therapeutically relevant concentration.

The results indicated that Compound 1 behaved similarly to propofol with respect to the 71 receptors and 16 enzymes tested. For example, Compound 1 and propofol each showed the greatest effect (greater than 30% inhibition of control binding) in the assay measuring picrotoxinin (active compound of picrotoxin) binding at the chloride channel isolated from rat cerebral cortex. This g-aminobutyric acid (GABA) ligand gated ion channel is a central target of action for propofol. Furthermore, Compound 1 and propofol each showed greater than 20% inhibition of control binding to only one of the 16 enzymes tested: phosphodiesterase 2 (PDE2). No significant effects were observed for alpha2, NMDA, PCP, benzodiazepine or opioid receptors.

EXAMPLE 8

Pain on Injection—Aqueous Phase Concentration

Injection pain, a common problem of propofol administration, is thought to be caused by propofol present in the aqueous phase of the lipid emulsion (see, e.g., Klement W et al, 1991, Br J Anaesth 67, 281). Several studies have reported a significant decrease in pain on injection when the aqueous phase concentration of propofol is reduced compared to the amount of propofol in the aqueous phase of DIPRIVAN (see, e.g. Doenicke A W et al, 1996, Anesth Analg 82, 472; Ueki R et al, 2007, J Anesth 21, 325).

The concentration of Compound 1 in the aqueous phase (aqueous phase concentration) of a lipid emulsion formulation was determined. This aqueous phase concentration was compared to that of propofol formulated in the same formulation and to that of DIPRIVAN® (AstraZeneca, Wilmington, Del., USA).

A one percent (1%) Compound 1 formulation was formulated in accordance with Example 4, Compound 1 being prepared as described in Example 5. A 1% propofol formulation was formulated in the same manner. DIPRIVAN (1% propofol injectable emulsion) was used as purchased from AstraZeneca.

The aqueous phase concentrations of Compound 1 and propofol were determined using the ultrafiltration method described by Teagarden DL at al., 1988, Pharmaceutical Research 5, 482. Briefly, four 0.4-ml samples of the 1% Compound 1 formulation, four 0.4-ml samples of the 1% propofol formulation, and two 0.4 samples of DIPRIVAN were placed in Ultrafree®-MC microcentrifuge filters (Millipore, Billerica, Mass.) and the aqueous phases separated from the lipid phases by microcentrifugation for 15 min at 5000 rpm. The concentrations of Compound 1 and propofol in the respective aqueous phases were quantified by liquid chromatography tandem mass spectrometry (LC/MS/MS) against standard curves of Compound 1 and propofol using thymol as an internal reference standard (analyses performed by Alturas Analytics Inc., Moscow. ID).

The aqueous phase concentration of Compound 1 in the 1% Compound 1 formulation was 0.38±0.02 μg/mL. The aqueous phase concentration of propofol in the 1% propofol formulation was 6.28±0.41 μg/mL. The aqueous phase concentration of propofol in DIPRIVAN was 4.1 μg/mL.

These results demonstrated a 94% reduction in the aqueous phase concentration of Compound 1 compared to that of propofol in identical formulations, and a 91% reduction in the aqueous phase concentration of Compound 1 compared to that of propofol in DIPRIVAN.

EXAMPLE 9

Pharmacokinetic Studies

Pharmacokinetic (PK) studies were conducted in domestic pigs to evaluate the pharmacodynamic effects of Compound 1 and to compare such effects to those of propofol.

A 1% Compound 1 formulation, prepared as described in Example 5 and formulated in accordance with Example 4, was administered to 6 pigs via a 20-min intravenous (IV) infusion at 0.380 mg/kg/min (7.6 mg/kg total dose) and to one pig at 0.456 mg/kg/min (9.12 mg/kg total dose). Plasma concentrations of Compound 1 were compared to historical propofol data generated per a similar protocol in which a 1% propofol formulation, formulated in the same manner as Compound 1, was administered to 5 pigs via a 10-min IV infusion at 0.750 mg/kg/min (7.5 mg/kg total dose).

Data from this study indicated that Compound 1 exhibited a similar pharmacokinetic profile to propofol in the pig model. A three-compartment model best described the Compound 1 and propofol data. Clearance of Compound 1 exceeded estimated hepatic blood flow, similar to propofol. Compound 1 also exhibited a similar metabolic pathway in pigs to that of propofol in humans: glucuronidation in the 1-position with the 4-position being subject to hydroxylation followed by glucuronide and sulfate conjugation. A dose-escalation study in dog showed similar plasma concentrations at washout for Compound 1 and propofol indicating similar clearance rates in that species as well.

EXAMPLE 10

Anesthetic Effects in Rats

The anesthetic dose response of bolus IV injection of Compound 1, compared to propofol, was studied in rats.

A validated rodent model of general anesthesia (see Hill-Venning C et al., 1996, Neuropharmacology 35, 1209: Lingamaneni R et al., 2001. Anesthesiology 94, 1050) was used to provide a measure of onset and duration of anesthesia as demonstrated by the Loss of Righting Reflex (LORR) and recovery time (time interval from return of righting reflex until the rat was able to grip and climb a steel frame and ambulate normally). Also measured was minimum dose to achieve LORR and maximum tolerated dose (MTD).

A 1% Compound 1 formulation, prepared as described in Example 5 and formulated in accordance with Example 4, or DIPRIVAN was administered by bolus IV injection at 2.5 ml/min to 6 male Sprague-Dawley rats (200-300 g) per dose group for the amount of time required to administer the doses described below. The relative potency was assessed by determining the dose required to cause 50% of the rats to lose righting reflex (HD50) and the dose required to produce 7 minutes of anesthesia (HD7 min). The ranges of doses studied were 1.9, 2.3, 3.0, 7.0, 13.7, 14.0 and 15.2 mg/kg for Compound 1 and 3.5, 4.0, 7.0 and 14.0 mg/kg for DIPRIVAN.

Results indicated that bolus IV administration of Compound 1 produced dose-dependent duration of anesthesia in rats. Onsets of LORR were less than 15 sec when the respective drugs were administered at a dose of at least 3.0 mg/kg for Compound 1 and at a dose of at least 7.0 mg/kg for propofol. Compound 1 produced no LORR at 1.9 mg/kg but did produce LORR at all other doses tested. Propofol produced no LORR in 4 of 6 rats tested at 3.5 mg/kg, but did produce LORR at all other doses tested. Table 1 compares the HD50, HD7 min, MTD, and therapeutic index (TI; defined herein as the ratio of MTD to HD7 min) results for Compound 1 and propofol. One rat died when administered 14 mg/kg DIPRIVAN. Two rats died when administered 15.2 mg/kg of Compound 1. Recovery time showed little relationship to dose except for high doses of Compound 1, which also produced prolonged LORR.

TABLE 1

Comparison of HD50, HD7min, MTD and TI results for Compound 1 and propofol administered by bolus IV to rats.

|  | Propofol | Compound 1 |
|---|---|---|
| HD50 | 3.8 mg/kg | 2.1 mg/kg |
| HD7min | 7.0 mg/kg | 2.3 mg/kg |
| MTD | <14 mg/kg | 14 mg/kg |
| TI | <2 | 6.1 |

In summary, Compound 1 showed potency at lower doses than propofol and also showed a higher MTD and improved TI compared to propofol.

(S,S)-2,6-di-sec-butylphenol, prepared in accordance with Example 2, was also evaluated in this test at doses of 2, 3, 4, 5, 6, 28, 35, 42, 49 and 56 mg/kg. Table 1a indicates HD50, HD7 min, MTD, and TI results for this compound. One of six rats died when administered 49 mg/kg of (S,S)-2,6-di-sec-butylphenol.

TABLE 1a

HD50, HD7min, MTD and TI results for (S,S)-2,6-di-sec-butylphenol administered by bolus IV to rats.

|  | (S,S) |
|---|---|
| HD50 | 4 mg/kg |
| HD7min | 5.2 mg/kg |
| MTD | 42 mg/kg |
| TI | 8.1 |

In a separate study, rats were administered 7 mg/kg of 1% Compound 1 in cremaphor or propofol, (S,S)-2-6-di-sec-butylphenol or (meso)-2-6-di-sec-butylphenol (prepared in accordance with Example 2) at the same doses and formulations. The results are shown in Table 1b. One of 6 rats administered 21 mg/kg of 1% (meso)-2-6-di-sec-butylphenol formulated in cremaphor died; however, the remaining 5 rats exhibited 34 min of anesthesia.

TABLE 1b

Comparison of duration of anesthesia (sleep time) for 7 mg/kg administrations of Compound 1, propofol, (S,S)-2-6-di-sec-butylphenol and (meso)-2-6-di-sec-butylphenol by bolus IV to rats.

|  | Sleep Time |
|---|---|
| Propofol | 7.1 min |
| Compound 1 | 23 min |
| (S,S) | 6.3 min |
| (meso) | 12.7 min |

In summary, the potency of (S,S)-2-6-di-sec-butylphenol was similar to propofol. The potency of (meso)-2-6-di-sec-butylphenol was improved compared to propofol. Both stereoisomers exhibited improved MTD and therapeutic indices compared to propofol.

EXAMPLE 11

Anesthetic and Hemodynamic Effects in Beagle Dogs

A dose-escalation study was conducted in dogs to demonstrate the anesthetic and hemodynamic effects of bolus IV administration of Compound 1 compared to propofol.

The endpoints for this study were dose relationship for induction, duration, depth and quality of anesthesia and hemodynamic effects of bolus IV administration of Compound 1 or propofol. A 1% Compound 1 formulation, prepared as described in Example 5 and formulated in accordance with Example 4, and a 1% propofol formulation formulated in the same manner were used.

Electroencephalographic (EEG) measurement of depth of anesthesia was measured with Bispectral Index (BIS), which is one of several systems used to measure the effects of anesthetic drugs on the brain and to track changes in the level of sedation or anesthesia. BIS is a mathematical algorithm that analyzes data from the EEG, and the output is a single number from 100 (fully conscious) to 0 (isoelectric EEG). Other assessments included sedation scores, clinical observations, blood pressure, electrocardiogram (ECG), and oxygen saturation.

Beagle dogs (male, 2-4 years old, 8-10 kg) were implanted with vascular access ports. At the time of implant surgery, the dogs' heads were shaved, marked for EEG electrode placement and injected with BOTOX® (Allergan, Inc. Irvine, Calif.; botulinum toxin type A purified neurotoxin complex):

40 units total per dog in 5 intramuscular (IM) injections across the brow were administered. The injections were intended to suppress muscular movement and electromyographic (EMG) interference with the BIS signal.

The study was a crossover design. Each dog received 2 to 4 escalating bolus IV doses (injected over 60 seconds) of Compound 1 or propofol separated by at least 30 min (or until the dog was awake) until the MTD was achieved. The MTD was defined as the dose that reduced mean arterial blood pressure (MAP) by 50% or to less than 50 millimeters of mercury (mmHg or mm Hg). All animals received supplemental oxygen and, if needed, ventilatory support after 4 min of apnea.

Depth of anesthesia was determined by assessing the presence or absence of lash reflex, response to glabellar tap or auditory stimulus, toe pinch, and breathing. Presence of each sign was scored as 1 and absence of each as 0. This allowed calculation of a Cumulative Sedation Score at multiple time points over the 30 min between doses (5=awake, 0=apneic/deep anesthesia). The quality of anesthesia was assessed by noting the smoothness of induction, qualitative assessment of muscle tone, and presence of involuntary motion. Episodes of involuntary movements (e.g. during emergence) were scored as present or absent throughout the observation period for each dose. BIS and hemodynamic effects were analyzed with 2-way ANOVA followed by t-test with Bonferroni correction for multiple comparisons of the effect of time and dose.

A. Anesthetic Effects

The abilities of Compound 1 and propofol administered by bolus IV to effect dose-related anesthesia in unpremedicated spontaneously breathing beagles (3.3-30 mg/kg/dose; 1-10 dogs per dose) are demonstrated in Table 2. Two of 3 dogs administered 15 mg/kg of propofol reached the MTD at 15 mg/kg. Therefore, only 1 dog was given the 30 mg/kg propofol dose.

TABLE 2

Dose-related duration of anesthesia (sleep time) for Compound 1 and propofol after bolus IV administration to dogs.

| Dose | Propofol | Compound 1 |
| --- | --- | --- |
| 5 mg/kg | 13 min | 24 min |
| 10 mg/kg | 28 min | 43 min |
| 15 mg/kg | 43 min | 77 min |
| 30 mg/kg | 69 min | 105 min |

The data also indicated that anesthesia was induced within 1 min at all doses for Compound 1 and propofol. Duration of anesthesia, measured by sleep time, was longer with Compound 1 than propofol at all doses. Cumulative sedation scores demonstrated approximately equipotent anesthetic depth for both propofol and Compound 1 above 5 mg/kg. There was no significant difference between BIS values for dogs administered Compound 1 at 10 mg/kg or propofol at 10 mg/kg or 15 mg/kg. Compound 1 produced a greater effect on BIS at doses of at least 15 mg/kg but these doses are very high, and potentially not clinically relevant. The quality of anesthesia (smoothness of induction, qualitative assessment of muscle tone, presence of involuntary motion) of Compound 1 was similar to propofol.

(S,S)-2,6-di-sec-butylphenol and (meso) 2,6-di-sec-butylphenol, produced in accordance with Example 2, were also evaluated in this test. Table 2a shows the dose-related duration of anesthesia (sleep time) for these compounds.

TABLE 2a

Dose-related duration of anesthesia (sleep time) for (S,S)-2,6-di-sec-butylphenol and (meso)2,6-di-sec-butylphenol after bolus IV administration to dogs.

| Dose | (S,S) | (meso) |
| --- | --- | --- |
| 5 mg/kg | 8 min | 25 min |
| 10 mg/kg | 24 min | 36 min |
| 15 mg/kg | 50 min | 55 min |
| 30 mg/kg | 50 min | 58 min |

The data also indicated that anesthesia was induced within 1 min at all doses for (S,S)-2,6-di-sec-butylphenol and (meso) 2,6-di-sec-butylphenol. Duration of anesthesia, measured by sleep time, was similar to propofol for (S,S)-2,6-di-sec-butylphenol and longer for (meso) 2,6-di-sec-butylphenol. The quality of anesthesia of (S,S)-2,6-di-sec-butylphenol was similar to propofol but was inferior for (meso) 2,6-di-sec-butylphenol.

B. Hemodynamic Effects: Blood Pressure

Hemodynamic data, such as mean arterial pressure (MAP), were recorded at baseline, 1, 2, 4, 8, 15, 20 and 30 min. Compound 1 was administered at 5, 10, 15 and 30 mg/kg to 3, 6, 6 and 3 dogs respectively. Propofol was administered at the same doses to 3, 5, 5, and 1 dogs, respectively. Only 1 dog received 30 mg/kg propofol because the MTD criteria were reached with 15 mg/kg in two animals. Data were analyzed with a 2-way ANOVA followed by t-test with Bonferroni correction for multiple comparisons.

A comparison of the data indicated that propofol produced a significantly greater effect on MAP than does Compound 1. Table 3 provides an example in which mean arterial pressure percent (MAP %) changes from baseline 4 min after bolus IV administration of 10, 15 or 30 mg/kg of Compound 1 are compared to MAP % changes effected by the same doses of propofol.

TABLE 3

Dose-related mean arterial pressures changes measured as MAP % change from baseline 4 min after bolus IV administration of Compound 1 or propofol to dogs.

| Dose | Propofol | Compound 1 |
| --- | --- | --- |
| 10 mg/kg | −22% | +11% |
| 15 mg/kg | −32% | −25% |
| 30 mg/kg | −66%* | −41% |

*Only 1 dog was tested at 30 mg/kg propofol in view of 2 dogs having reached the MTD criteria at 15 mg/kg propofol.

(S,S)-2,6-Di-sec-butylphenol and (meso)-2,6-di-sec-butylphenol, produced in accordance with Example 2, were also evaluated in this test. A comparison of the data indicated that propofol produced a significantly greater effect on MAP than do (S,S)-2,6-Di-sec-butylphenol or (meso)-2,6-di-sec-butylphenol. Table 3a provides an example, comparing MAP % changes from baseline at 4 min.

TABLE 3a

Dose-related mean arterial pressures changes measured as MAP % change from baseline 4 min after bolus IV administration of (S,S)-2,6-Di-sec-butylphenol and (meso)-2,6-di-sec-butylphenol to dogs.

| Dose | (S,S) | (Meso) |
| --- | --- | --- |
| 10 mg/kg | +7% | +5% |
| 15 mg/kg | +5% | +15% |
| 30 mg/kg | 0% | −16% |

EXAMPLE 12

Anesthetic and Hemodynamic Effects in Mongrel Dogs

This study compared the effect of total intravenous anesthesia in chronically instrumented mongrel dogs administered Compound 1 or propofol. Assessments included hemodynamic performance parameters such as blood pressure, heart rate, and cardiac output as well as clinical chemistry parameters and EEG analysis.

A 1% Compound 1 formulation, prepared as described in Example 5 and formulated in accordance with Example 4, and DIPRIVAN (1% propofol injectable emulsion) were compared in adult (at least 9 months old; approximately 20-40 kg) mongrel dogs.

General anesthesia was induced in the dogs by IV administration of 7 mg/kg DIPRIVAN, and the dogs were tracheally intubated and mechanically ventilated. General anesthesia was maintained using 2.2% end-tidal sevoflurane in oxygen. A thoracotomy was performed at the fifth left intercostal space, and heparin-filled catheters were placed in the proximal descending thoracic aorta (P50 pressure transducer Gould, Oxnard, Calif.), and in the right and left atria to provide IV access. An ultrasonic transit-time flow probe (T108, Transonic Systems, Ithaca, N.Y.) was placed around the ascending thoracic aorta. A 20 kHz Doppler flow probe (Model HDP-20-3.5, Triton Surgical Technologies, San Diego, Calif.) was placed around the left anterior descending coronary artery. Six MHz sonomicrometer crystals (Hartley, Houston, Tex.) were implanted in the subendocardium. A high fidelity micromanometer (P7, Konigsberg Instruments, Pasadena. CA) was inserted into the left ventricle. A hydraulic vascular occluder (In Vivo Metric Systems, Healdsburg, Calif.) was positioned around the thoracic inferior vena cava. Instrumentation was exteriorized, the chest wall was closed in layers, and the pneumothorax was evacuated. The dogs recovered a minimum of 7 days before experimentation and were acclimated to standing in a sling during the recovery period.

The dogs were fasted overnight. Conscious dogs were placed in a sling, and needle electrodes were inserted to record Lead II ECGs. Scalp electrodes were positioned to record EEGs (MP150, Biopac Systems, Goleta, Calif.) in 3 bipolar recording configurations that sampled frontal, temporal, parietal, and occipital regions. The dogs then received a 500 ml IV bolus of normal saline, following which an IV infusion of normal saline was established at a rate of 3 ml/kg/hr (60-120 ml/hr per dog) for the duration of the experiment. The dogs were allowed to stabilize for 30 minutes. EEG was recorded continuously during the experiment. Arterial blood gas and chemistry measures included pH, $pO_2$, $sO_2$, $pCO_2$, $tCO_2$, carbonate, potassium, sodium, and base excess, and were measured immediately following blood draws using a blood gas and chemistry analyzer (ABL-505, Radiometer, Copenhagen). Blood clinical chemistry measurements included albumin, albumin/globulin ratio, alkaline phosphatase, ALT (SGPT), AST (SGOT), bicarbonate, direct bilirubin, BUN. BUN/creatinine ratio, calcium, chloride, cholesterol, CK, creatinine, globulin, glucose, phosphorus, potassium, sodium, sodium/potassium ratio, and total protein. Following stabilization, baseline measurements of EEG, hemodynamics, ECG, and blood gases were recorded. Blood samples were drawn for PK and clinical chemistry, and pressure volume loops were generated and data recorded.

Immediately following baseline measurements, the dogs received a 4 mg/kg (1 dog) or 5 mg/kg (6 dogs) IV bolus dose of Compound 1 or a 7 mg/kg IV bolus dose of propofol (7 dogs) over 1 minute to induce general anesthesia. Following induction, the dogs were tracheally intubated, and mechanically ventilated using 50% oxygen in nitrogen throughout the subsequent drug infusion and recovery periods. Beginning 4 minutes after the end of the bolus dose, the dogs that received the Compound 1 bolus were administered a series of four 15-minute IV infusions at rates of 0.25, 0.5, 1.0 and 2.0 mg/kg/min of Compound 1 in a stepwise crossover fashion; the same protocol was used for dogs receiving the propofol bolus except that propofol was infused at the indicated rates and times. MAP was monitored continuously, and dosing was discontinued immediately if MAP decreased below 50 mmHg at any time or if the heart rate increased over 200 beats per minute. Dosing was halted in one dog at the end of the 1.0 mg/kg/min Compound 1 infusion period and in two others during the 2.0 mg/kg/min Compound 1 infusion period. At the end of each 15-minute infusion, measurements of EEG, hemodynamics, ECG, and blood gases were recorded, blood samples were drawn for PK, and pressure volume loops were generated and data recorded. Following dosing, the dogs were allowed to recover. Ventilation was discontinued, and the trachea extubated, when subjective interpretation of clinical observations indicated sufficient recovery from general anesthesia. Time of tracheal extubation was noted. At 30 minutes after the end of the final infusion, measurements of EEG, hemodynamics, ECG, and blood gases were recorded, blood samples were drawn for PK, and pressure volume loops were generated and data recorded. Concentrations of Compound 1 and propofol in dog plasma were determined, and concentrations of 5 metabolites (1 oxidative, 3 glucuronide-conjugated, and 1 sulfate-conjugated) were estimated, using liquid chromatography (LC) and tandem mass spectrometry (MS/MS) (performed at Alturas Analytics).

Results indicated that arterial blood gas and clinical chemistry data were stable. EEG analysis showed dose-related sedative-hypnotic effect and no evidence of seizure or pre-seizure activity. All dogs recovered from general anesthesia at a similar rate regardless of whether they had been administered Compound for propofol. Compound 1 and glucuronide metabolites in both the 1-position and the 4-position were detected in the plasma. Plasma concentrations were consistent with the drug administration regimen.

In this model, at therapeutically relevant doses, EEG results showed a greater anesthetic potency effect for Compound 1 compared to propofol. There were no statistically significant differences between MAP and heart rate results for Compound 1 and propofol. Cardiac output in propofol-treated dogs was significantly reduced from baseline; in contrast, Compound 1-treated dogs exhibited no statistically significant reduction in cardiac output.

EXAMPLE 13

Anesthetic and Hemodynamic Effects in Pigs

Anesthetic and hemodynamic effects of Compound 1 and propofol were compared in anesthetized ventilated pigs infused IV with a 1% Compound 1 formulation, prepared as described in Example 5 and formulated in accordance with Example 4, or DIPRIVAN (1% propofol injectable emulsion). Assessments included EEG measurements of depth of anesthesia using BIS, pharmacokinetics, blood pressure, ECG, heart rate, cardiac output, body temperature, and oxygen saturation.

Experiments were performed on commercial farm-bred swine of either sex (mean weight 33.6 kg). Anesthesia was induced with isoflurane. Intravascular access was obtained from an ear vein. Each pig was intubated and mechanically ventilated. Tissue oxygenation was monitored using continuous pulse oximetry placed on the tongue. Ventilation was monitored using an inspired/expired gas analyzer that measured oxygen, carbon dioxide, and potent inhalation agent concentrations. Ventilator settings were adjusted as needed to maintain steady state.

A continuous level of anesthesia was achieved with isoflurane and an infusion of pancuronium (10 mg/hr). ECG was monitored throughout the study. Arterial blood pressure was monitored through the cannulated left femoral artery. MAP, systolic and diastolic arterial pressures and heart rate were collected every 5 seconds. An internal jugular vein was cannulated with a pulmonary artery catheter for thermodilution estimates of cardiac output and blood temperature. Body temperature was maintained at 37° C. Instrumentation for EEG monitoring was accomplished using an adhesive electrode array over the fronto-occipital regions (Aspect Medical. Norwood, Mass., USA).

The experimental design included a 30 min stabilization period, followed by IV infusion of Compound 1 (0.384 mg/kg/min×20 min) or propofol (0.750 mg/kg/min×10 min. The respective infusion was followed by a 180 min washout period. Hemodynamic measurements and blood samples for pharmacokinetic analysis were taken at pre-infusion, every 2 min during infusion of Compound 1 or propofol and at frequent intervals during the washout period. The infusion times and rates for Compound 1 and propofol were previously determined to produce a maximum reduction of BIS (<10) during the infusion period. Arterial blood samples for determining pH, pO2, pCO2, glucose, potassium, and lactate were measured at baseline before Compound 1 or propofol infusion, during infusion, and hourly after infusion.

Metabolic and hemodynamic parameters for each group were compared at multiple time points using an unpaired two-tailed Student t test. To account for multiple comparisons and maintain the probability of a type I error below 0.05, P values less than 0.025 were considered significant.

A. Anesthetic Effects

Compound 1 and propofol produced maximal suppression of BIS (<10) with IV infusions of 14.7±3.8 min of 384 µg Compound 1 per kg per min and 9.4±1.9 min of 750 µg propofol per kg per min, respectively. The effect on EEG was reversible and returned to baseline within 60 min. The area under the curve (AUC) of Compound 1 required to reach maximum pharmacodynamic effect (Emax) was significantly smaller than that for propofol (51.5±15.5 versus 108.7±24.3 µg-min/mL, respectively). In conclusion, the data indicated that Compound 1 was more potent than propofol.

B. Hemodynamic Effects

Figure 2:
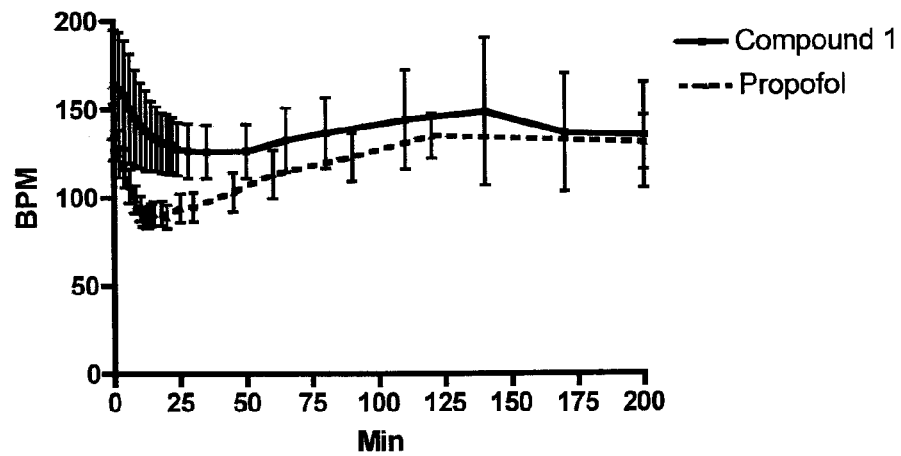
FIG. 2 shows the effect on heart rate (beats per minute) in pigs following IV infusion of the (−) stereoisomer of formula (I) in which X is H in comparison with propofol.
Figure 3:
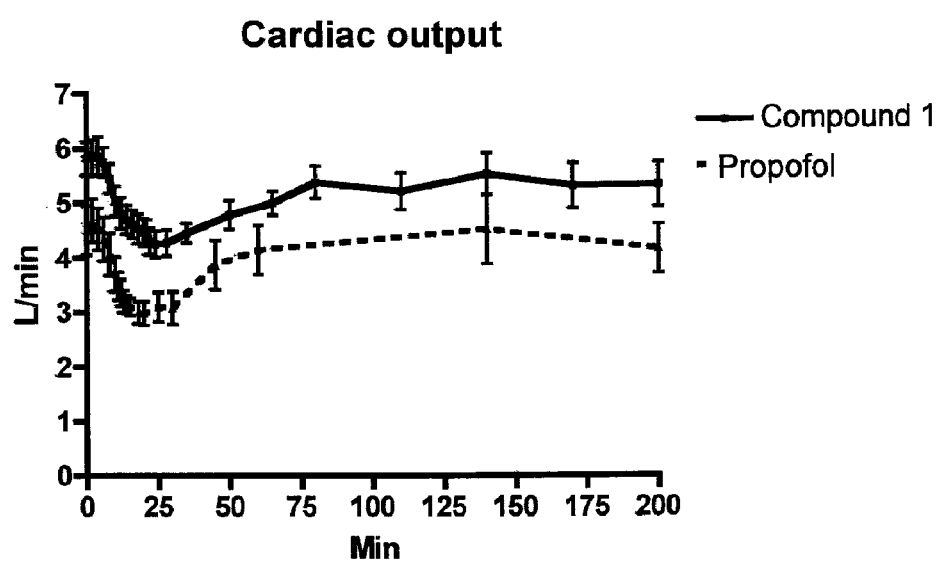
FIG. 3 shows the effect on cardiac output (liters per minute, or L/min) in pigs following IV infusion of the (−) stereoisomer of formula (I) in which X is H in comparison with propofol.

Mean arterial pressure and heart rate were measured at intervals throughout IV infusion and washout with Compound 1 (0.384 mg/kg/min, 5 pigs) and propofol (0.750 mg/kg/min. 6 pigs). Results are shown in FIGS. 1 and 2 respectively. FIG. 3 compares cardiac output produced by Compound 1 compared to propofol. Arterial blood gas samples from pigs infused with Compound 1 were taken and analyzed for blood gas and serum chemistry values; mean values are reported in Table 4.

TABLE 4

Arterial blood gas and serum chemistry mean values.

| Min | pH | pC02 | pO2 | ABEc | Potassium | Glucose | Lactate |
|---|---|---|---|---|---|---|---|
| 0 | 7.4861 | 38.8 | 390 | 5.6 | 3.80 | 99.6 | 1.43 |
| 4 | 7.5027 | 37.2 | 410 | 5.8 | 3.71 | 102.9 | 1.24 |
| 20 | 7.5066 | 36.8 | 419 | 5.7 | 3.84 | 102.0 | 1.20 |
| 80 | 7.4943 | 37.5 | 402 | 5.4 | 4.00 | 99.7 | 1.01 |

TABLE 4-continued

Arterial blood gas and serum chemistry mean values.

| Min | pH | pC02 | pO2 | ABEc | Potassium | Glucose | Lactate |
|---|---|---|---|---|---|---|---|
| 140 | 7.4803 | 37.2 | 399 | 4.1 | 4.10 | 100.7 | 0.95 |
| 200 | 7.4641 | 37.6 | 356 | 3.2 | 4.06 | 102.4 | 0.96 |

ABEc refers to acid base excess, corrected.

Baseline MAP and HR values were not different between Compound 1 and propofol. Both compounds reduced MAP, but propofol produced a significantly larger decrease in MAP (66±4) than did Compound 1 (106±3) (p<0.001). The lowest HR measured for propofol (88±6 bpm) was significantly lower than the lowest FIR measured for Compound 1 (129±6 bpm) (p<0.5). Both MAP and FIR returned to baseline after discontinuation of infusions of Compound 1 or propofol. There was no significant difference in the reduction of cardiac output produced by Compound 1 compared to propofol.

Table 4 indicates that all arterial blood gas and serum chemistry values were within normal limits: Compound 1 did not produce any significant metabolic alterations such as metabolic acidosis or increased lactate.

EXAMPLE 14

Anti-emetic Activity

Compound 1 was tested for its anti-emetic potential in ferrets and compared to that of propofol.

Male descented ferrets weighing 1.0-1.5 kg with vascular access ports in the jugular vein were housed on a 12/12-hour light/dark cycle under controlled temperature, with food and water provided ad libitum. On each study day, food was presented to ferrets one hour prior to dosing. Immediately prior to dosing, food and water were removed. A 1% Compound 1 formulation, prepared as described in Example 5 and formulated in accordance with Example 4, or DIPRIVAN was administered by IV infusion to the ferrets; see Wynn R L et al, 1993, Eur J Pharmacol 241, 42 re DIPRIVAN administration in ferrets. After administration of Compound 1 or DIPRIVAN, animals were placed in clean, transparent cages (with lids) and left unrestrained for a 45-min observation period by an observer blinded to the specific treatment administered.

Emesis in ferrets is characterized by rhythmic abdominal contractions that are associated either with the oral expulsion of solid or liquid material from the gastrointestinal tract (i.e., vomiting) or with movements that do not include passage of material (i.e., retching). Episodes of retching and/or vomiting were considered separate episodes when the interval between retches and/or vomits exceeded 5 sec.

Pro-emetic activity of Compound 1 or propofol was studied in 6 ferrets per drug as follows: Ferrets were anesthetized by isoflurane inhalation. Compound 1 or propofol was administered by an IV infusion for 15 min at 1 mg/kg/min. After termination of the infusion, the ferrets were observed continuously for 45 min, and the number of vomits and retches were counted.

Anti-emetic activity of Compound 1 or propofol was studied in 6 ferrets per drug as follows: Ferrets were anesthetized with isoflurane, administered Compound 1 or propofol by a 15 min IV infusion at 1 mg/kg/min. After termination of the infusion, 0.5 mg/kg morphine sulfate was administered subcutaneously and the ferrets were monitored for 45 min as described above. Six additional ferrets were administered subcutaneously 0.5 mg/kg morphine sulfate only.

Morphine sulfate (0.5 mg/kg) alone was pro-emetic in ferrets, yielding 15 episodes of vomiting and 157 retches. Compound 1 did not produce any episodes of vomiting or retching when administered alone or in the presence of morphine. Ferrets that received propofol and morphine sulfate exhibited 3 vomits and 47 retches. Therefore, Compound 1 and propofol both reduced the incidence of vomiting and retching in the presence of morphine.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A (−)-stereoisomer of formula (I):

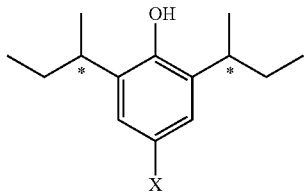

wherein X is H or F; or a salt or prodrug thereof.

2. A compound as claimed in claim 1, which is a (−)-stereoisomer of formula (I) or a pharmaceutically acceptable salt or prodrug thereof.

3. A compound as claimed in claim 2, which is a (−)-stereoisomer of formula (I) or a pharmaceutically acceptable salt thereof.

4. A compound as claimed in claim 1, in which X is H.

5. A pharmaceutical composition comprising a compound as claimed in claim 2, and a pharmaceutically acceptable carrier.

6. The pharmaceutical composition of claim 5 which is formulated for intravenous administration.

7. The pharmaceutical composition of claim 6 which is formulated as a lipid emulsion.

8. A method for inducing or maintaining general anesthesia in an animal comprising administering to the animal an effective amount of a (−)-stereoisomer of formula (I):

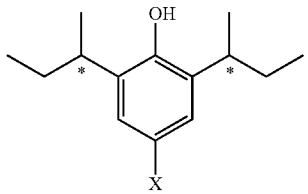

wherein X is H or F; or a pharmaceutically acceptable salt or prodrug thereof.

9. A method as claimed in claim 8, in which X is H.

10. A method as claimed in claim 8, comprising administering to the animal an effective amount of a (−)-stereoisomer of formula (I) in which X is H, or a pharmaceutically acceptable salt thereof.

11. A method for promoting sedation in an animal comprising administering to the animal an effective amount of a (−)-stereoisomer of formula (I):

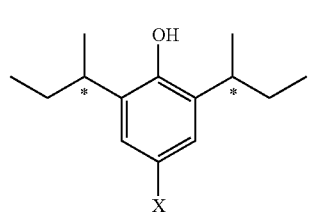

wherein X is H or F; or a pharmaceutically acceptable salt or prodrug thereof.

12. A method as claimed in claim 11, in which X is H.

13. A method as claimed in claim 11, comprising administering to the animal an effective amount of a (−)-stereoisomer of formula (I) in which X is H, or a pharmaceutically acceptable salt thereof.

14. A process for preparing a (−) stereoisomer of formula (I)

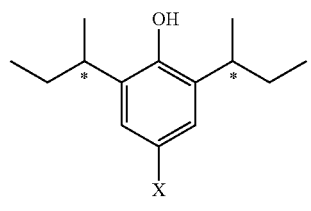

wherein X is H or F; or a salt or prodrug thereof, which comprises hydrolysing a carbamic acid (−)-2,6-di-sec-butylphenyl ester diastereomer of formula:

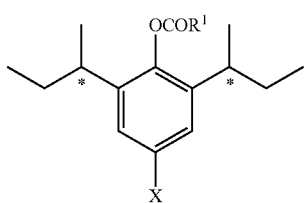

in which $R^1$ represents a chiral amino group, and wherein X is H or F, followed if required by forming the free phenol or salt or pro-drug thereof.

15. A carbamic acid (−)-2,6-di-sec-butylphenyl ester diastereoisomer of formula

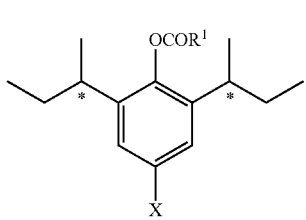

in which $R^1$ represents a chiral amino group, and in which X is H or F.

16. A diastereoisomer as claimed in claim 15, which $R^1$ represents an (R)-1-arylethylamino group.

17. A compound as claimed in claim 2, in which X is H.

18. A compound as claimed in claim 3, in which X is H.

19. A method for inducing or maintaining general anesthesia in an animal comprising administering to the animal an effective amount of a compound of claim 3.

20. The method of claim 19, wherein X is H.

21. A method for promoting sedation in an animal comprising administering to the animal an effective amount of a compound of claim 3.

22. The method of claim 21, wherein X is H.

23. The process of claim 14, wherein the salt is a pharmaceutically acceptable salt.

24. The process of claim 14, wherein X is H.

25. The process of claim 14, wherein the process comprises forming the free phenol or salt or pro-drug thereof.

26. The process of claim 25, wherein X is H.

27. The process of claim 25, wherein the process comprises forming the free phenol or pharmaceutically acceptable salt or pro-drug thereof.

28. The process of claim 27, wherein X is H.

29. The process of claim 27, wherein the process comprises forming the free phenol or pharmaceutically acceptable salt.

30. The process of claim 29, wherein X is H.

31. The process of claim 29, wherein the process comprises forming the pharmaceutically acceptable salt.

32. The process of claim 31, wherein X is H.

33. The pharmaceutical composition of claim 5, wherein X is H.

34. A pharmaceutical composition comprising a compound of formula (I):

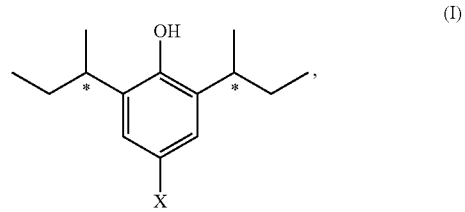

wherein the compound is a (−)-stereoisomer of formula (I) and wherein X is H or F; or a pharmaceutically acceptable salt thereof and a pharmaceutically acceptable carrier.

35. The pharmaceutical composition of claim 34, wherein X is H.

36. The pharmaceutical composition of claim 34, which is formulated for intravenous administration.

37. The pharmaceutical composition of claim 36, which is formulated as a lipid emulsion.

* * * * *